(12) United States Patent
Sid

(10) Patent No.: US 9,058,739 B2
(45) Date of Patent: Jun. 16, 2015

(54) ELECTROMECHANICAL SWITCH FOR CONTROLLING TOXIC GAS

(71) Applicant: Alberto Sid, Upper Saddle River, NJ (US)

(72) Inventor: Alberto Sid, Upper Saddle River, NJ (US)

(73) Assignee: Fumes Safety LLC, Lido Beach, NY (US)

( * ) Notice: Subject to any disclaimer, the term of this patent is extended or adjusted under 35 U.S.C. 154(b) by 313 days.

(21) Appl. No.: 13/629,847

(22) Filed: Sep. 28, 2012

(65) Prior Publication Data

US 2013/0021119 A1    Jan. 24, 2013

Related U.S. Application Data

(62) Division of application No. 11/700,668, filed on Jan. 31, 2007, now Pat. No. 8,286,603.

(51) Int. Cl.
| | |
|---|---|
| *H01H 9/20* | (2006.01) |
| *G08B 21/14* | (2006.01) |
| *B60K 28/10* | (2006.01) |
| *F23N 5/24* | (2006.01) |
| *G01N 33/00* | (2006.01) |

(52) U.S. Cl.
CPC .......... *G08B 21/14* (2013.01); *H01H 2300/018* (2013.01); *B60K 28/10* (2013.01); *F23N 5/24* (2013.01); *G01N 33/004* (2013.01); *G01N 33/0063* (2013.01)

(58) Field of Classification Search
CPC ................................................ H01H 2300/018
See application file for complete search history.

(56) References Cited

U.S. PATENT DOCUMENTS

| | | | | |
|---|---|---|---|---|
| 2,510,789 | A | * | 6/1950 | Wright ........................ 290/37 R |
| 3,946,204 | A | * | 3/1976 | Taniguchi et al. ............. 235/435 |
| 2003/0090849 | A1 | * | 5/2003 | Simms et al. .................. 361/115 |

FOREIGN PATENT DOCUMENTS

CN          202441962 U  *  9/2012

* cited by examiner

*Primary Examiner* — Mohamad Musleh
(74) *Attorney, Agent, or Firm* — James R. Klaiber; Pryor Cashman LLP

(57) ABSTRACT

An electromechanical switch comprising a plunger, a first switch in contact with the plunger in a first position of the plunger, in which a connection of the switch is open, a button in sliding contact with the plunger, and a solenoid in contact with the plunger in a second position of the plunger, in which a connection of the first switch is closed.

5 Claims, 23 Drawing Sheets

| Function | RED LED | Flash type | Unit Status |
|---|---|---|---|
| Normal | ON | | Normal, AC and good battery |
| Normal | FLASHES | Slow | Normal, NO AC, good battery |
| CO alarm | FLASHES | RAPID | Initiating CO alarm |
| Low battery | FLASHES | Every minute | AC powered, low battery |
| Error | FLASHES | 3 chirps/minute | bad unit |
| Test | FLASHES | RAPID | Test/Reset button pressed |

FIG.2

| Function | GREEN LED | RED LED | Unit Status |
|---|---|---|---|
| Normal | ON | OFF | Normal, AC and good battery |
| Normal | FLASHES | OFF | Normal, NO AC, good battery |
| CO alarm | don't care | OFF | Initiating CO alarm |
| CO alarm | don't care | FLASHES | CO alarm - danger |
| Low battery | ON | FLASHES | AC powered, low battery |
| Error | don't care | FLASHES | bad unit |
| Error | don't care | ON | bad unit |
| Test | ON | FLASHES | Test/Reset button pressed |

FIG. 3

| Function | GREEN LED | AMBER LED | RED LED | Unit Status |
|---|---|---|---|---|
| Normal | ON | OFF | OFF | Normal, AC and good battery |
| Normal | FLASHES | OFF | OFF | Normal, NO AC, good battery |
| CO alarm | don't care | ON | OFF | Initiating CO alarm |
| CO alarm | don't care | don't care | FLASHES | CO alarm - danger |
| Low battery | ON | OFF | FLASHES | AC powered, low battery |
| Error | don't care | don't care | FLASHES | bad unit |
| Error | don't care | don't care | ON | bad unit |
| Test | ON | ON | FLASHES | Test/Reset button pressed |

FIG. 4

ELECTROMECHANICAL SWITCH FOR CONTROLLING TOXIC GAS

This divisional application claims priority to prior filed U.S. non-provisional application Ser. No. 11/700,668 filed Jan. 31, 2007. All description, drawings and teachings set forth therein are expressly incorporated by reference herein and claim to priority upon the teachings expressly made herein.

TECHNICAL FIELD OF THE INVENTION

The present disclosures relate to a system and method of controlling the concentrations of one or more gases in a space. More specifically, the present disclosure relates to a system and method for preventing and controlling the concentration of gaseous products or byproducts, such as carbon monoxide (CO), in a space when a predetermined concentration is exceeded by interrupting the process, such as combustion, which produces the gases.

BACKGROUND OF THE INVENTION

The combustion or processing of certain materials often results in the production of certain gases. When the concentration of these gases exceeds a predetermined threshold, it may be desirable to cease the combustion or processing which is directly or indirectly producing the gas. One such gas is carbon monoxide. Carbon monoxide is a colorless, odorless, tasteless gas, which is produced through an incomplete combustion of a hydrocarbon. Carbon monoxide can be produced by various fuel burning appliances, such as, fuel fired furnaces, gas hot water heaters, gas stoves, gas dryers, space heaters, vehicles, snow blowers, portable power generators, etc.

Once present, this gas circulates freely throughout a building, such as a home. If this gas is not ventilated properly, carbon monoxide poisoning may result. Carbon monoxide inhibits the blood's ability to carry oxygen to body tissue, including vital organs such as the heart and brain. When carbon monoxide is inhaled, it combines with oxygen-carrying hemoglobin of the blood to form carboxyhemoglobin. Once combined with the hemoglobin, the hemoglobin is no longer available for transporting oxygen. The amount of carboxyhemoglobin that builds up is a factor of the concentration of the gas being inhaled and the duration of the exposure. Carbon monoxide can act in the body in high concentrations, or slowly over a long period of time. Because it takes several hours to remove carbon monoxide from the body of a person, concentrations of carbon monoxide can gradually build up in the blood causing headaches, fatigue, dizziness, nausea, burning eyes, or unconsciousness.

Sources of Carbon Monoxide (CO)

Carbon monoxide can be produced whenever a hydrocarbon is burned and the combustion is incomplete. Hydrocarbons include all fossil fuels and their derivations, such as oil, natural gas, gasoline, coal, etc. Sources of carbon monoxide include power generators and other gasoline powered equipment; un-vented kerosene and gas space heaters; leaking chimneys and furnaces; back-drafting from furnaces, and others. Incomplete oxidation during combustion in gas ranges and non-vented gas or kerosene heaters may cause high concentrations of CO in indoor air. Worn or poorly adjusted and maintained combustion devices (e.g., boilers, furnaces) can be significant sources of CO.

Standards or Guidelines

According to the inventor's understanding, no standards for CO concentration have been agreed upon for indoor air. However, CO detectors/alarms always have been and still are designed to alarm before potentially life-threatening levels of CO are reached. The UL standard 2034 (1998 revision) has stricter requirements that the detector/alarm must meet before it can sound. As a result, the possibility of nuisance alarms is decreased. UL-2034 standard calls for the following levels and actions:

70 PPM—alarm between 60 & 240 minutes
150 PPM—alarm between 10 & 50 minutes
400 PPM—alarm between 4 & 15 minutes

Carbon Monoxide (CO) Detectors

Because carbon monoxide is a colorless, odorless, tasteless gas, it virtually impossible to detect its presence without a carbon monoxide detector. Devices for sensing carbon monoxide and triggering an audible and/or visual alarm in the presence of excess concentrations of carbon monoxide are presently available and their use is known to those of ordinary skill in the art. The most common types of CO sensors used in CO detectors are described below.

A biomimetic type (chem-optical or gel cell) sensors works with a form of synthetic hemoglobin which darkens in the presence of CO, and lightens without it. This can either be seen directly or connected to a light sensor and alarm.

Electrochemical-type sensors are a type of fuel cell that, instead of being designed to produce power, is designed to produce a current that is precisely related to the amount of the target gas (in this case carbon monoxide) in the atmosphere. Measurement of the current therefore gives a measure of the concentration of carbon monoxide in the atmosphere. Essentially the electrochemical cell consists of a container, 2 electrodes, connection wires and an electrolyte—typically sulfuric acid. Carbon monoxide is oxidized at one electrode to carbon dioxide whilst oxygen is consumed at the other electrode. For carbon monoxide detection, the electrochemical cell has advantages over the other technologies in that it has a highly accurate and linear output to carbon monoxide concentration, requires minimal power as it is operated at room temperature, and has a long lifetime (typically commercial available cells now have lifetimes of 5 years or greater). Until recently, the cost of these cells and concerns about their long term reliability had limited uptake of this technology in the marketplace although these concerns are now largely overcome.

The electrochemical-type sensor type is the example used for explaining embodiments of the invention below. Typically the cell used generated a current of 45 nA/ppm (nano amperes per part per million of carbon monoxide) for example, a concentration of 85 ppm in the area will create a current equal to (45 nA/ppm×85 ppm)=3.825 uA (micro Amperes). This current can be easily converted to voltage by using a high precision resistor, and then measured by an A/D (analog to digital) converter either external to, or built in the microcontroller as explained below.

In a semiconductor-type detector, thin wires of the semiconductor tin dioxide wafer on an insulating ceramic base provide a sensor monitored by an integrated circuit. CO reduces resistance and so allows a greater current which if high enough will lead to the monitor triggering an alarm. This sensor is more expensive and less used in residential CO detectors.

Generators

In the majority of the portable gas powered generators available in the retail and commercial markets today, the mechanism used shorts one lead of the ignition module to ground (which is normally the generator's metal frame and body of the alternator) in order to shut down the gas engine. This is true for both manually cranked gas engines (pull rope) and electrically cranked, larger engines (sealed lead acid batteries or electric starter—such as of those used in larger generators and snow throwers). For battery or electrically cranked engines, there are two switches, one mostly called RUN/STOP and the other for cranking the engine, normally a momentary pushbutton called START. There are certain generators and engines that both of these switches may be combined into one, three position switch. The positions will then be STOP-RUN-START, being the START position a momentary position.

Microcontrollers

The term microcontroller as used herein includes microcontrollers, microprocessors, and the like. Microcontrollers are highly integrated devices that execute a stored program. The program is stored as a series of instructions, usually in non-volatile memory. Microcontrollers often use external resonators or crystals to supply clock pulses that paces the microcontroller. Instructions may take one, two, or more clock cycles to be executed depending on the design of the microcontroller.

SUMMARY

A safety system for connection to a toxic gas detector and a toxic gas producing engine, and its operating method, includes an interrupt device coupled to connections to the detector and the engine. The interrupt device includes a toxic gas signal detecting circuit and a circuit for permitting starting of the engine. The detecting circuit activates the permitting circuit if the toxic gas signal represents a toxic gas concentration below a predetermined level. In one embodiment, the permitting circuit is activated if the safety system is healthy and fully functional.

Similarly, a safety system for connection to a toxic gas detector and a toxic gas supply, and its operating method, includes an interrupt device coupled to connections to the detector and the toxic gas supply. The interrupt device includes a toxic gas signal detecting circuit and a circuit for permitting of flow from the toxic gas supply. The detecting circuit activates the permitting circuit if the toxic gas signal represents a toxic gas concentration below a predetermined level.

BRIEF DESCRIPTION OF DRAWINGS

FIG. 2 shows the different status indication on a detector having one light emitting diode (LEDs).

FIG. 3 shows the different status indication on a detector having two light emitting diodes (LEDs).

FIG. 4 shows the different status indication on a detector having three light emitting diodes (LEDs).

DETAILED DESCRIPTION

Figure 1:
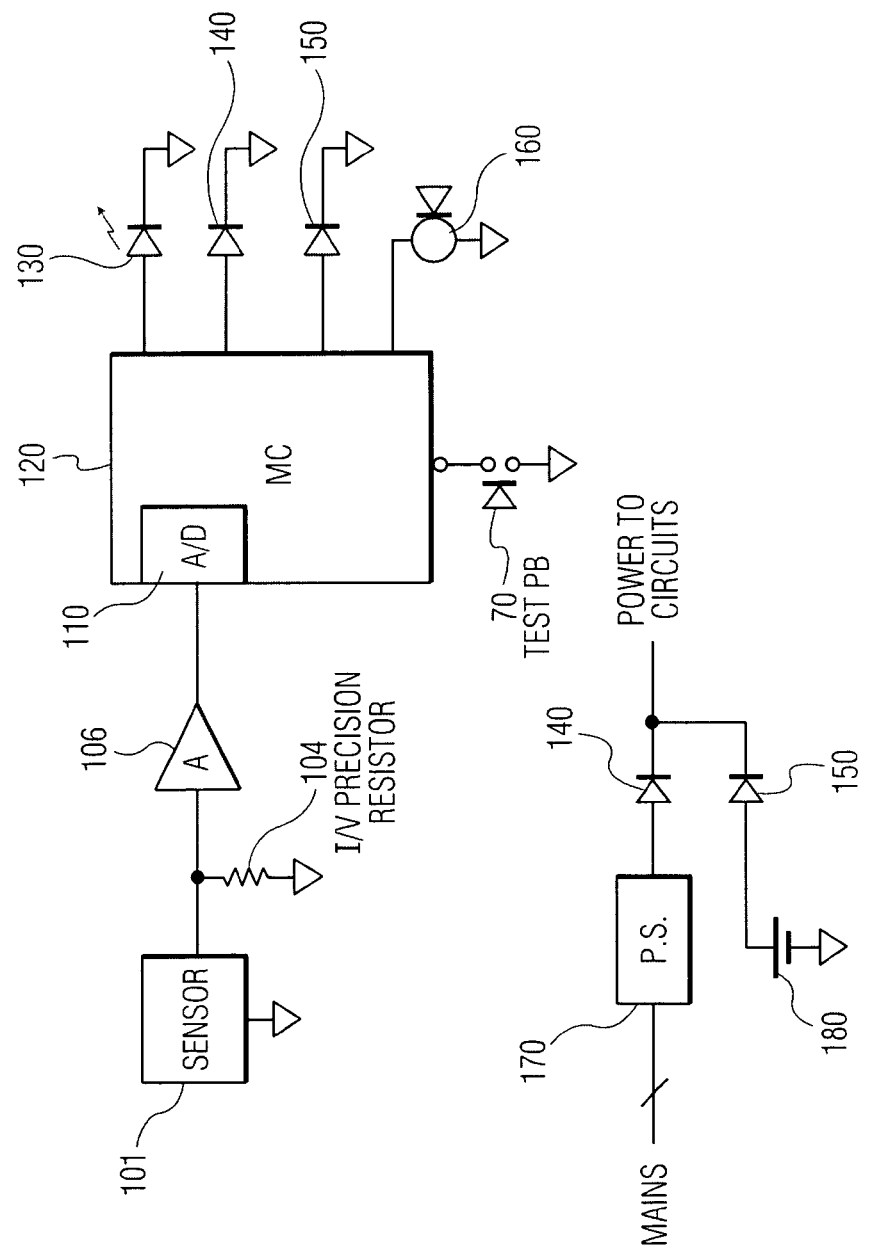
FIG. 1 shows the block diagram of a typical gas detection unit, in this example a typical CO detector.

There are reported and existing cases of people improperly operating power generators indoors without proper ventilation, which resulted in fatalities. A method and device to detect dangerous levels of CO and effectively shutdown the gas engine was developed, tested and successfully installed in portable power generators which will remedy this situation.

Embodiments of the invention use a variety of methods to interface to the gas engine without interfering with its normal operation, and without modifications to the engine, or alternator. This system monitors the emission of CO in the vicinity of the power generator. Once it detects dangerous concentrations of CO, it effectively shuts down the engine. The engine cannot be restarted until the level of CO drops down. The preferred embodiment has the capability of minimizing false shutdowns. Many scenarios were properly considered to encompass normal operational ways of the power generators, while contemplating and understanding erroneous operations of the generator that may lead to lethal consequences. An audible alarm and visual alarm indicator (flasher) for the hearing impaired has been also incorporated in the preferred embodiment. In addition to shutting down the appliance, both these alarms will be set until they are manually silenced. In the course of explaining embodiments of the invention, different ways to interface to different CO or commercial gas detectors are described. These detectors are used as a building block for the detection of the toxic gases. There are many companies (for example Kiddie, First Alert, etc) with extensive expertise in minimizing false alarms, analyzing and properly responding to different levels and timing of toxic gases concentrations. These units often run proprietary software algorithms.

All detectors of toxic gases, such as smoke, CO, propane, etc monitor the quality of the air by using a dedicated sensor. Each type of sensor may have a different structure and use a different mechanism to react to different gases. For illustrative purposes, CO sensors are described.

There are several known detection mechanisms for toxic gases that alarm in case that the level of the gas being sampled exceeds a predetermined threshold. This is the typical CO or smoke detector. Once the threshold is exceeded an audible or visual alarm (or both) will be activated. There are also devices that will trigger auxiliary devices too, but they all fail in showing how to interface and effectively shut down the gas engine while eliminating changes to the engine itself.

One aspect of embodiments of the invention is the logic of detecting and shutting down the engine or appliance generating the toxic gas. Conventional detectors may alarm or trigger only if toxic levels are detected. In embodiments of this invention, the device or appliance will work only in the absence of the toxic gas. Thus, the ignition mechanism will only be active if there is no toxic level of gas detected, as opposed to actuating a shutdown mechanism if toxic levels are detected. The engine (in the case of power generator) will not be able to be started if the safety unit is malfunctioning, or disconnected, or the batteries powering the safety device and or gas detector are removed.

Power generators will generate power once they are started. Embodiments of this invention use the power generated by the generator to power the electronic control, sensor, circuitry, safety shutdown, etc. In order to use this approach, the engine will have to be able to be started. Once started, the generator will generate power to power the CO detector and interrupt mechanism. This means that before the engine is started, the safety detection circuitry will not be functional, which presents a problem.

Also, if the alternator (the unit that generates the power) is faulty, for example due to a tripped fuse, or a bad/open/ shorted winding, the generator will not generate power, therefore disabling the CO detector safety device, allowing the engine to be run possibly with potentially dangerous consequences, such as when run inside a residence, confined spaces or poorly ventilated areas.

In other words, a gas powered generator that uses its self generated power to monitor and actuate a safety device will disable its own safety monitoring and detection if for any reason or failure it will fail to generate power, although the gas engine will continue to effectively run and possibly generate toxic levels of gases. Thus, the health of the electrical power generated is monitored, and the system is shut down if the electrical portion fails.

Embodiments of the invention use a backup battery (similar to the electrically powered detectors with backup batteries). This backup battery is used to allow the engine to be started and run. In embodiments of this invention, the generator will not be able to be started if high concentrations of CO are detected, or if the batteries powering up the system are no good, or have been removed, or have been wrongly inserted.

In embodiments of the invention, once the generator starts generating power, the safety device will be powered by the generator, thus conserving the batteries. Rechargeable batteries can also be used here, being recharged when the generator is running.

If the alternator fails (will not generate power), embodiments of the invention will revert to battery backup to continue monitoring the presence of the toxic gas(es). If the batteries don't provide power to run the safety mechanism, or it malfunctions, or the batteries are removed during the operation of the generator, embodiments of the invention (due to the reverse logic used here) will shut down the engine regardless of the level of gas being monitored.

Certain embodiments of the invention include a working safety device to enable the operation of the appliance, as well as a good battery. So long as there is no power to the safety device, the appliance, or power generator, will not be able to be started.

In the case of a POWER SWITCH (as in the case of main switches to be used in furnace rooms, boiler rooms, etc) using embodiments of the invention, there is no need for backup batteries, since absence of power will mean shutting down the appliance, such as a furnace, or heater, etc. In the case of this switch, there will be no backup battery.

If toxic levels of the monitored gas are detected, embodiments of the invention will not only disable the cause of the toxic gas but sound an audible alarm or flasher for the hearing impaired, so people in the vicinity of the toxic gas can move out until the room can be properly ventilated.

Carbon monoxide and toxic gas detectors have been developed, used and improved for many years. Originally passive logic (transistors, diodes and other passive components) were used in conjunction with gas sensors of different types as described here; buzzers, flashers and even voice integrated circuits to monitor, trigger and alert in case of toxic concentrations of gas are known to the public.

Latter implementations, as presently used in residential and commercial detection units, use microcontrollers, as taught in U.S. Pat. Nos. 6,819,252 and 5,828,822 (incorporated by reference) to monitor the gas sensor's unit, calculate the concentration levels and compare to a predetermined threshold level. If this threshold is exceeded, the alarm sounds. Different types of software algorithms, such as taught in U.S. Pat. No. 7,142,105 (incorporated by reference), have been developed and used. There are many different types of CO detection units in the market. What sets them apart is the type of algorithms used in order to minimize false alarms, and trigger according to the outlines and specifications of UL-2034 (Revision October 1998) which sets the level of toxic and dangerous levels of carbon monoxide, as well as the response time of the alarm according to different concentrations.

Embodiments of this invention use existing, readily available CO, smoke, and toxic gas detectors as a building block to implement the above safety devices, switches, etc. Specifically, and for the purpose of explaining the method, an implementation of the safety unit for gas powered generators using commercial CO detectors is described.

Embodiments of this invention use and interface to the RUN/STOP switch discussed above, where the ignition is shorted to ground to stop the engine. When the generator's RUN/STOP switch is on the RUN position, it is electrically open, and the engine can be started and run; when the switch is in the STOP position, it is electrically closed; the generator's engine is then shut down if it was running, or it cannot be started if it was stopped. All the examples, implementations and explanations below are based on this type of switch.

Figure 15:
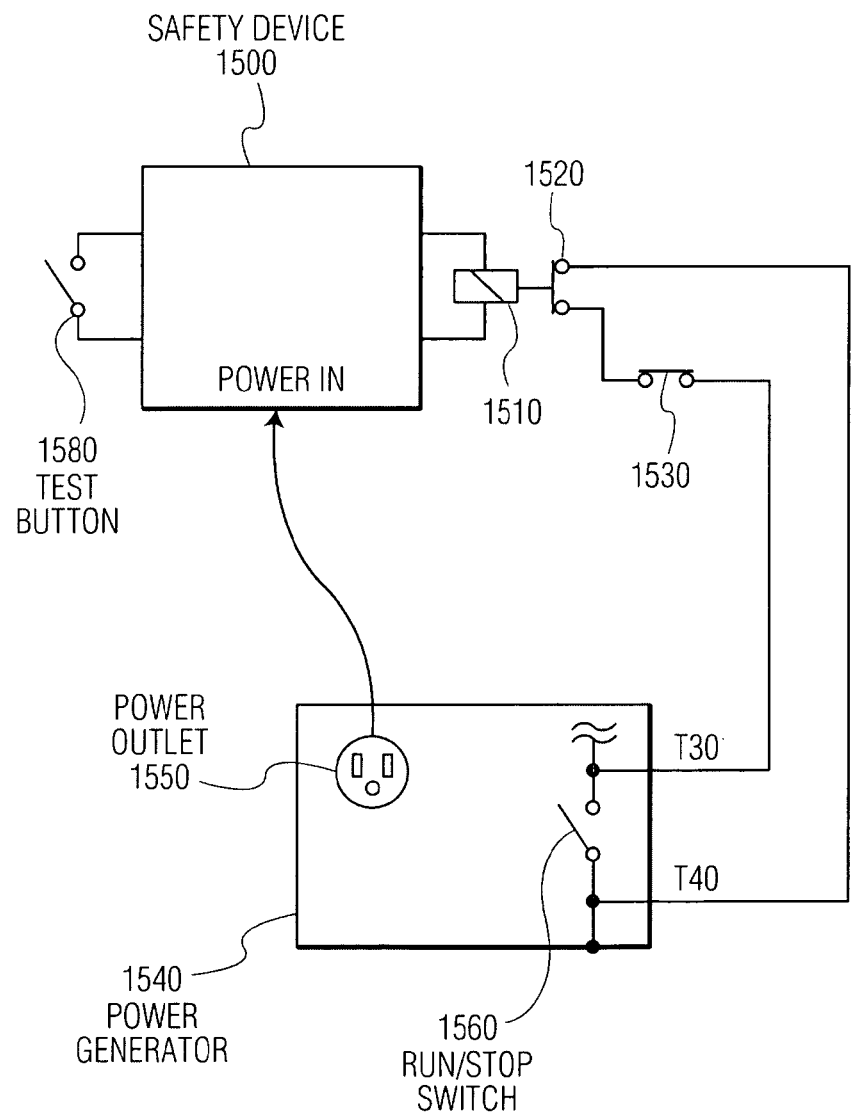
FIG. 15 shows an implementation with a commercial mains-powered CO detector without a battery backup and electromechanical switch.

If this mechanism is reversed on a different type of generator (such as in order to run the generator, a set of contacts is electrically shorted; and in order to stop the generator, the electrical path is open), a change that may be needed in certain embodiments of the invention is to use instead of a NORMALLY CLOSED relay (or solid state relays (SSRs)) such as relay 1510 and SAFETY SHUTDOWN terminals T30 and T40 in FIG. 15, a NORMALLY OPEN type relay or SSR.

Embodiments of the invention detect carbon monoxide emissions while operating portable gas powered generators. During the reduction to practice, other embodiments and uses became apparent.

These embodiments and uses include:

1—Kerosene heaters; these portable heaters, have a mechanical tripping mechanism that retracts the wick if a mechanical movement or shift is detected, such as a person trying to move the heater during combustion. By using embodiments of the invention, the same mechanism may be tripped. The poisonous gas can be not only CO but, for example, a low level of oxygen in the ambient, or smoke, or a combination. This application is discussed in more detail below.

2—Water heaters; detection of CO or propane gas (weather natural or liquid) can also be implemented by using embodiments of the invention. If the system detects an unsafe level of CO, or propane, or any dangerous gas, or a combination, it will automatically shutdown the gas supply to the heater. This application is discussed in more detail below.

3—Heating furnaces; as in the case of the water heater, if unsafe levels of poisonous gas(es) is (are) detected, the unit can effectively shutdown the furnace, in this case, by interrupting the electrical supply to the furnace. The unit can obviously shut down the gas supply to the furnace as well, but in this case, there is always a delay from the time the gas supply is interrupted, to the time that the main blower is shutdown. This is to allow the circulation of cold air thru the heating plenum, to avoid expansion/contraction of the plenum and early cracking. In the case of presence of a poisonous gas, it may be undesirable to simply shutdown the gas supply, since the gas will then be distributed thru the venting system. In this case, it is preferred to shut down the electrical power to the furnace, and therefore cutting immediately the circulation and further distribution of the poisonous gas. U.S. Pat. No. 6,339,379 (incorporated by reference) teaches a carbon monoxide detector for detecting the level of carbon monoxide in a furnace supply duct. The control unit provides a signal to the limiting switch upon detection of a carbon monoxide level above a pre-determined level whereby the limiting switch is activated to shut off the furnace. Embodiments of invention differ from this because the electrical supply and or gas is shut down as explained herein. Also, the unit explained herein, may be installed in the furnace's room rather than in the furnace's supply duct. This application is discussed in more detail below.

4—Gas space heaters—non-vented—as in the case of Rinnai space heaters. These heaters do not vent the combustion gases to the outside environment. This is also a typical application where the heaters can be equipped with this type of safety device as in the case of furnaces, where it is advisable to abruptly interrupt the electrical and or gas supply to the heater in the presence of CO or low levels of oxygen. These units are becoming extremely popular due to its simple, "local" installation, as opposed to central air conditioned systems; also used as retrofits in places were originally electrical wall heaters were installed on the early '70's. This application is discussed in more detail below.

5—Another excellent application is a power switch (wall switch) which will interrupt, or "trip" upon the presence and detection of a poisonous gas. This type of switch can then be used as the mains supply switch for boiler rooms, furnace rooms, etc. etc. It s important to understand that this is a straight replacement, and can be installed by simply replacing the typical "emergency switch" for gas and furnaces, often located at the top of stairs in basement on in the vicinity of furnaces. This application is discussed in more detail below.

6—Portable BBQ's, heaters and other appliances using gas cylinders (bottles) that can be run inside confined spaces. Embodiments of the invention may be used to interrupt the flow of gas to the BBQ, heater or appliance once dangerous levels of toxic gases are detected. The unit can be built and sold as a retrofit kit, to be installed between the gas bottle and the gas connector of the BBQ, heater or appliance. This application is discussed in more detail below.

FIG. 1 shows the construction of a typical gas detection unit, (for example a CO detector). Sensor 101 monitors the presence of a certain gas in the environment. Its current output (as explained above in detail) is proportional to the level of that gas mixed with the air. Once this current is circulated thru precision resistor 104 it is then converted into a voltage across it. This voltage is therefore proportional to the level of the gas detected by sensor 101. Operational amplifier 106 amplifies the level of this voltage to a higher voltage, so as it can be read by analog to digital converter A/D 110 (this A/D can be either external or internally contained in the microcontroller). In addition, operational amplifier 106 converts the high impedance output of the sensor into a lower impedance so A/D 110 connection load won't affect the output of sensor 101. Microcontroller 120 is responsible for monitoring the levels of gas (translated as a digital reading from A/D outputs 110). It also monitors the presence of mains power, as well as the health of backup battery 180. Led 130 represents GREEN LED, led 140 represents AMBER LED, led 150 represents RED LED, all to indicate certain statuses as denoted in FIG. 4. It is important to note that these three LEDs can be combined into one or two LEDs (as indicated in FIGS. 2-3) to indicate the status of the detecting unit. Buzzer 160 is an audible device used to alert of a dangerous level of toxic gas detected by sensor 101, as well as to indicate the presence of mains power, low battery, and unit's malfunction. TEST/RESET pushbutton 70 has a double function, as in most of the commercial CO alarm units. If the safety device is in a non-alarm mode (no dangerous levels of CO detected) depressing TEST/RESET pushbutton will cause microcontroller 120 to simulate an alarm, and go into an alarm mode. If gas detector is in an alarm mode, depressing TEST/RESET pushbutton 70 causes the audible alarm 160 to be silent, but still keeps status indicator(s) LED(s) 130, 140, and 150 active.

FIG. 2 is a table showing the different situations and visual status of a typical commercial CO detection unit, having a single LED indicator, which is usually but not necessarily red. Such type of detector is manufactured by First Alert under model No. CO-605. Note that more advanced CO detectors (such as First Alert Model FCD4) may use a digital display readout but still will have at least one LED to indicate the status according to the status table.

FIG. 3 is a table showing the different situations and visual status of a typical commercial CO detection unit, having two LED indicators, one is usually but not necessarily red to indicate alarm or attention statuses (such as a low battery) and usually but not necessarily green indicator to indicate the status of power, i.e. if the units is receiving electricity from the mains.

FIG. 4 is a table showing the different situations and visual status of a typical commercial CO detection unit, having three LED indicators, one is usually but not necessarily red to indicate alarm or attention statuses (such as a low battery) and usually but not necessarily green indicator to indicate the status of power, i.e. if the units is receiving electricity from the mains. The third LED is usually but not necessarily AMBER or YELLOW, and it is used to indicate when levels of the toxic gas are increasingly high and the detector is arming for triggering an alarm.

By closely analyzing and comparing FIG. 2, FIG. 3 and FIG. 4 it is clear that all possibilities in the detection and alarming of dangerous toxic levels of CO as well as low, missing batteries, loss of electrical power, test mode and or unit's malfunction, are covered and indicated by the status of the column denoted as RED LED of FIGS. 3 and 4. For the case of a single LED alarm unit, as in FIG. 2 all above cases are also covered by the single LED. For embodiments of the present invention, therefore, the status of this LED may be monitored and accordingly reacted to.

Figure 5:
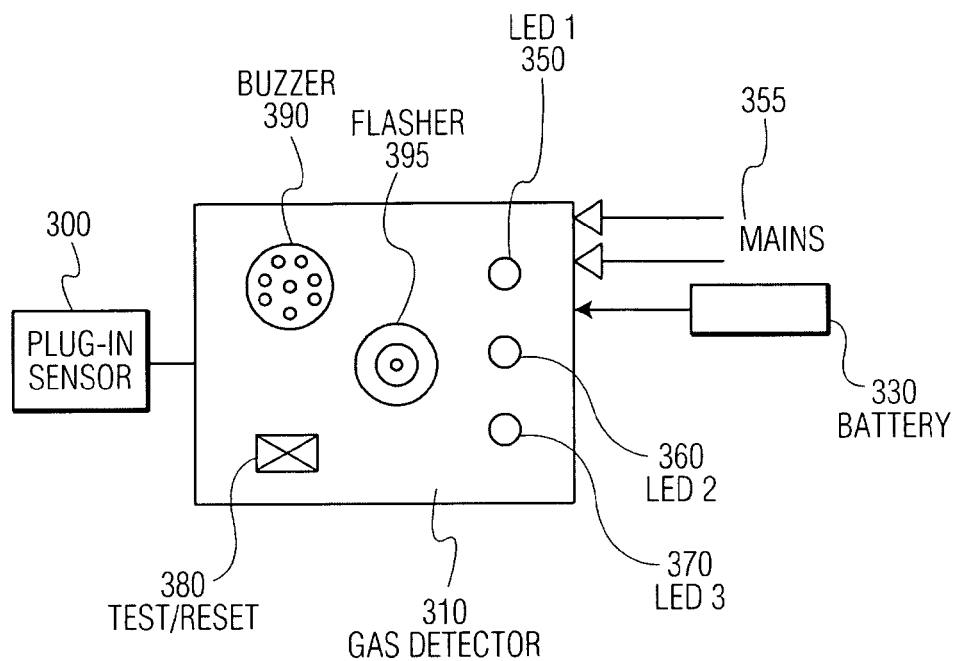
FIG. 5 shows a gas detector with a plug in replaceable sensor.

FIG. 5 shows a gas detector with a plug-in replaceable sensor. CO detector 310 houses a socket where toxic gas sensor 300 plugs into. CO detector 310 has at least one LED 350 to indicate status of detector. It may also have two or three LEDs as explained elsewhere, and denoted as LEDs 360 and 370. Buzzer 390 is an audible alarm to indicate the presence of high levels of toxic gases as well as low battery indication. Flasher 395 is an option to attract attention for the hearing impaired. Detector plugs into electrical mains 355, and it has a battery backup 330 that powers the detector in case of power failures. TEST/RESET pushbutton 380 is a dual function switch. If the detector is normally operating in a non-alarm condition, by depressing it causes the detector to simulate a high CO or toxic gas level alarm. It also tests the proper functioning of all the electronics. If gas detector 310 is in an alarm mode, by depressing TEST/RESET pushbutton 380 causes the audible alarm to be silent, but still keeps status indicator(s) LED(s) 350, 360, and 370 active. Note that by changing the replaceable sensor, 300, different toxic gases can be detected with basically the same detector unit 310. Similarly, multiple sensors (which may be replaceable) may be used to detect different unsafe toxic gas situations, such as CO and ammonia, and or other toxic gases.

This plug-in sensor has electronics built-in in order to standardize its output so it can be interfaced to a "common" detector base 310 having the same functions as outlined in FIGS. 2, 3, and 4. For example, if a CO sensor with an output of 45 nA/ppm is used (as explained above) the sensor may be built using electronics to standardize, say, to 1 Volt/ppm of CO. In a similar way, a sensor may detect another toxic gas with a standardized output of 1 Volt/ppm of that toxic gas. This way the same safety device may be used with different sensor probes in different applications.

Figure 6:
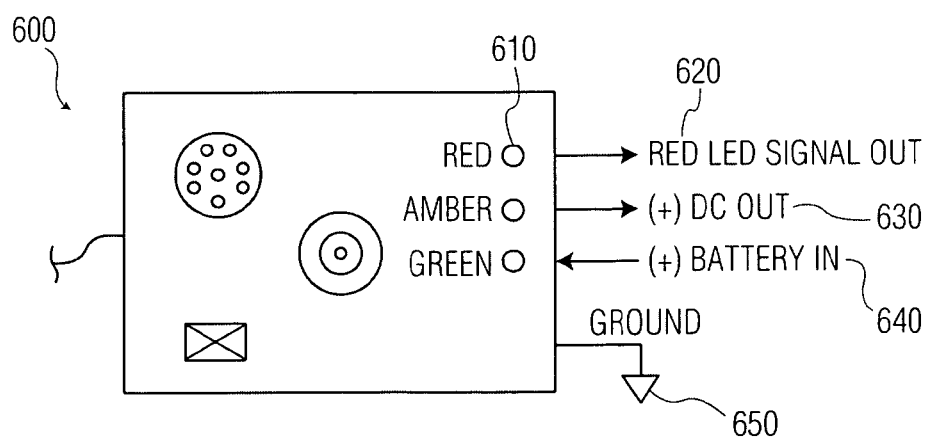
FIG. 6 shows the signals used by embodiments of the invention to interface to a commercial CO detector.

FIG. 6 shows the signals from a commercial CO detector that may be used to interface with embodiments of the invention. Gas detector 600 is any commercial toxic gas (such as CO) detection unit, such as and similar to the described in FIG. 5, which has either one, two or three status LEDs. For the case of a single LED detector, alarm LED 610 will be used to generate LED signal out 620. In the case of two or three LEDs alarm units, the signal called "RED LED" in last column of FIG. 3 and FIG. 4 is used. This signal may also be obtained from the positive terminal of the buzzer in the detector, or through an optocoupler physically attached and aligned to detect the light generated by the RED LED, or through an acoustic sensor that receives the noise generated by the buzzer. Main-power-operated CO alarms may have an internal power supply similar to those described in FIG. 7 or FIG. 8. Signal (+) DC OUT 630, is derived from signal 730 or 780 (depending on the type of power supply used in the specific CO detector) of the detector's internal power supply, as well as signal GROUND 650, which is derived from signal 740 or 790 (depending on the type of power supply used in the specific CO detector) of the detector's internal power supply. Signal (+) BATTERY IN 640 is the positive terminal of the backup battery of the CO detector, and it can be obtained from the detector's battery holder.

For explanation purposes, two typical internal power supply topologies used to rectify the AC mains and convert to DC to power the electronics of the detector are shown. Other topologies exist as understood by those of skill in the art.

Figure 7:
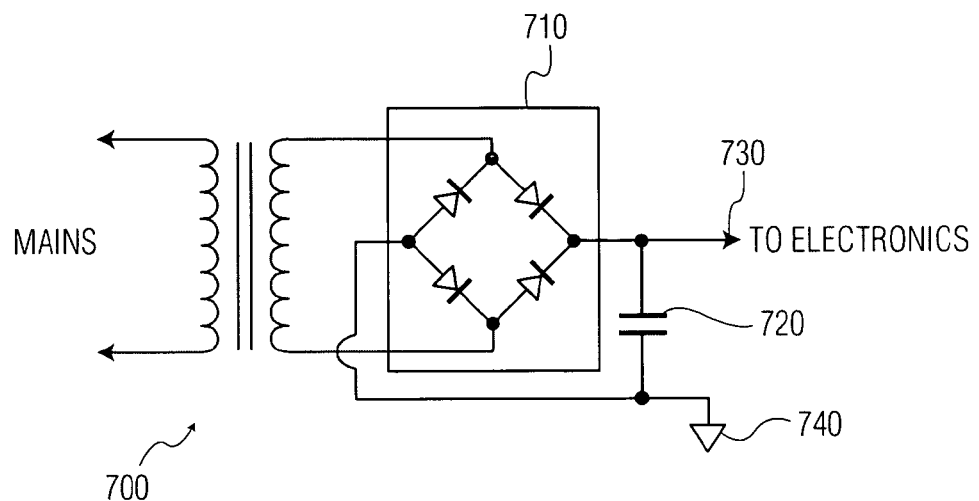
FIG. 7 shows a typical internal mains-powered power supply of a commercial CO detector.

FIG. 7 is a typical internal power supply in commercial CO detectors. Transformer 700 is connected to mains power line. Low voltage side of transformer 700 is connected to a full bridge rectifier 710 which rectifies the AC output of transformer 700. Electrolytic capacitor 720 filters the rectified DC output of bridge rectifier 710 in order to obtain a clean, low ripple DC voltage. Voltage signal 730 and ground signal 740 can be used to interface to embodiments of the invention.

Figure 8:
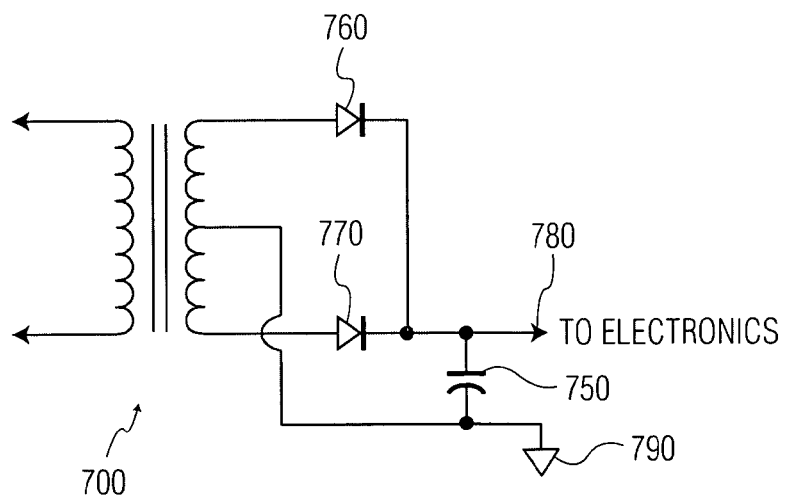
FIG. 8 shows yet another typical internal mains-powered power supply of a commercial CO detector.

FIG. 8 is yet another typical internal power supply in some commercial CO detectors. Transformer 700 is connected to mains power line. Low voltage side of transformer 700 is connected to rectifier diodes 760 and 770 which rectify the AC output of transformer 700. Electrolytic capacitor 750 filters the rectified DC output in order to obtain a clean, low ripple DC voltage. Voltage signal 780 and ground signal 790 can be used to interface to embodiments of the invention.

Figure 9:
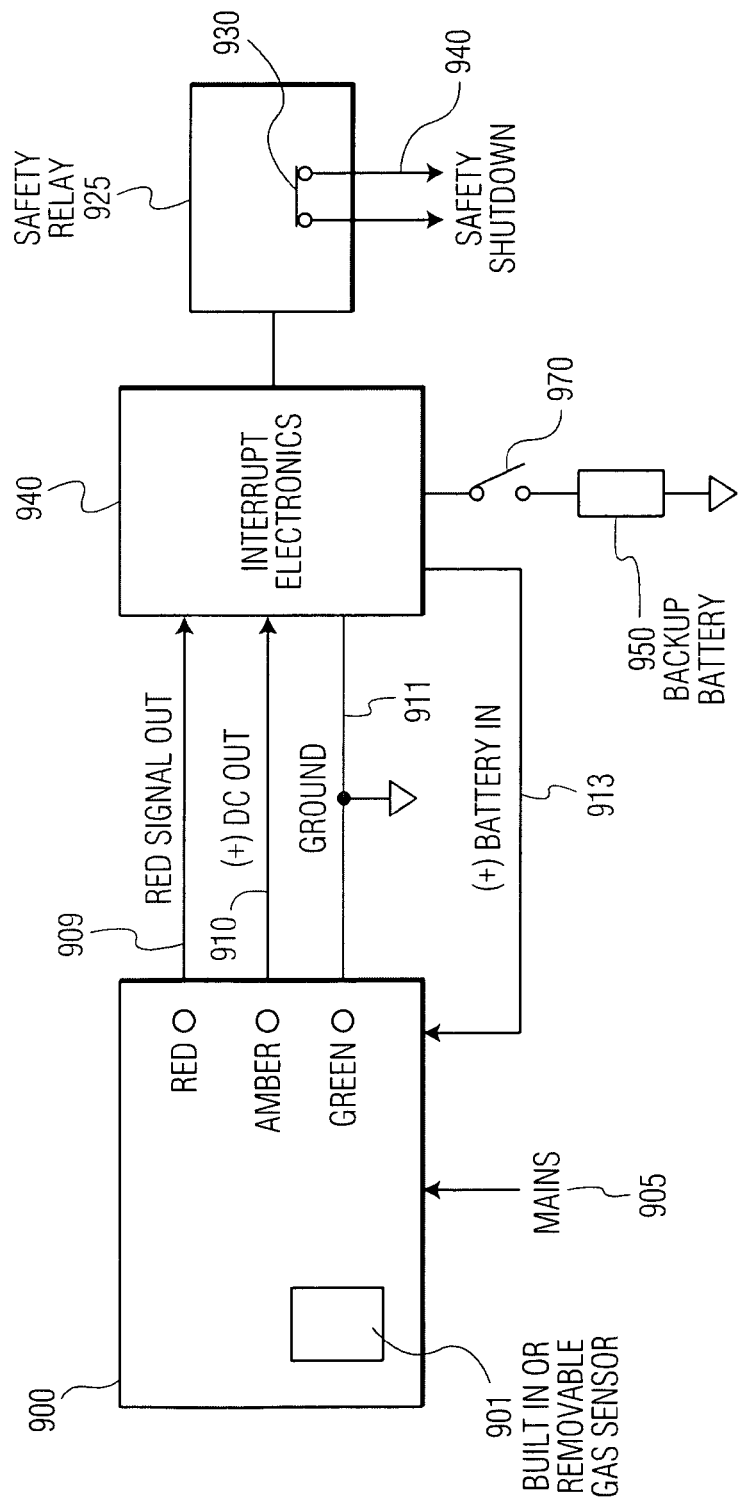
FIG. 9 shows a block diagram of an embodiment of the invention.

FIG. 9 is a block diagram of an embodiment of the invention, where a CO detection unit 900 has an internal or removable gas sensor 901, and plugs into main power by means of a built-in plug or terminal strip or other type of connector 905. Backup battery 950 powers the detector and electronics when there is no power from the main (such as in the case of the portable generators, when the generator is not running). RED SIGNAL OUT 909, (+) DC OUT 910, GROUND 911 and (+) BATTERY IN 913 are the interface signals from/to the CO detector 900 and obtained as explained in FIG. 6 and above. Interrupt electronics 940 contains the electronics to analyze, properly react and activate safety relay 925 in response to RED LED signal condition as specified in FIGS. 2, 3, and 4.

Battery backup 950 runs the detector 900 as well as the electronics 940. Power switch 970 disables all the electronics and also functions as the RUN/STOP switch for the portable power generators. Safety NORMALLY CLOSED (NC) relay 925 is normally de-energized, and therefore NORMALLY CLOSED contacts 930 are shorted when there is no power to the system.

Portable gas power generators often use a switch that normally lets the gas engine run when the contacts of this switch are open. In other words, to start the engine the switch needs to be electrically open, and to shut down the engine, it shorts the two wires, or, as in most if not all the portable generators in the market, to ground, or frame ground (the metal frame where the generator is housed). Embodiments of the invention replace (or connect in parallel, as shown later) the RUN/STOP switch by means of contact 930 in safety relay 925 thru electrical wires 940. Note than in the case of a safety switch, for example in a furnace's safety switches, this contact can be normally open and when the relay is energized, the contacts are closed, enabling the flow of electricity to the furnace, boiler room or other such systems as understood by those of skill in the art.

Figure 10:
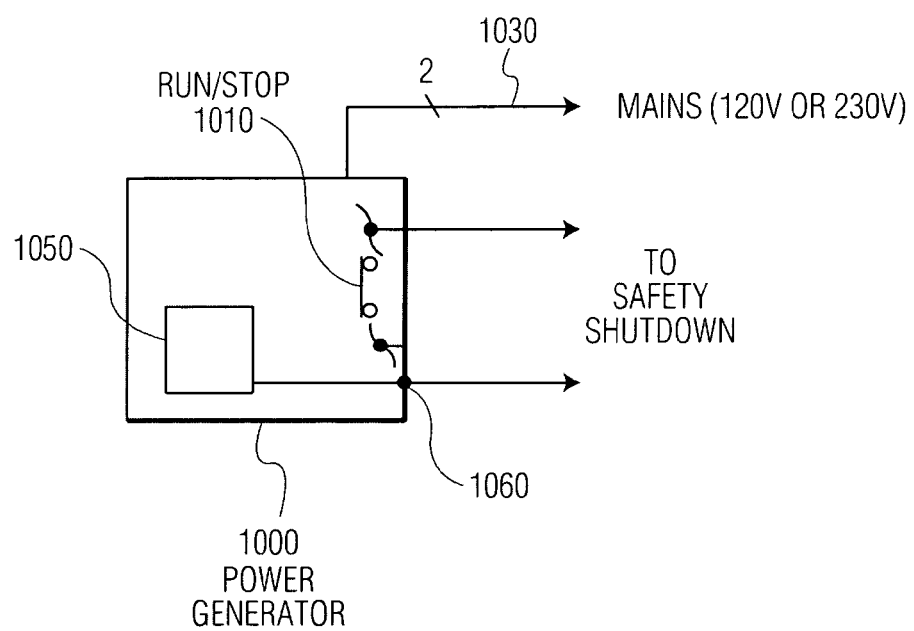
FIG. 10 shows the interfacing signals to a portable gas generator.

FIG. 10 shows how an embodiment of the invention interfaces to a portable power generator 1000. Portable power generators have a RUN/STOP built in switch 1010. This switch, when open (RUN position), lets the gas engine run by enabling the ignition module of the gas engine to run. When shorted to ground, the engine stops (STOP position). The operation of ignition module of the gas powered engines may be any module operable in this configuration.

By simply connecting SAFETY SHUTDOWN contacts 930 in FIG. 9 in parallel to RUN/STOP switch 1010 (thru electrical wires 940) the operation of the gas engine may be controlled externally. RUN/STOP switch 1010 is thus left open (RUN position on the generator), disconnected or totally removed, since now power switch 970 of FIG. 9 will now control the RUN/STOP function.

It is important to note that in many portable power generators, one lead of the RUN/STOP switch 1010 is connected to the main frame of the power generator 1000, which is also electrically connected to the ground of alternator 1050, forming a GROUND connecting point 1060. In this case, the interfacing of embodiments of the invention to the generator is even simpler, by connecting to the main frame (ground) and the other lead to the ignition module. So, embodiments of the invention connects the power generator to the main, ground, and RUN/STOP signal.

Figure 11:
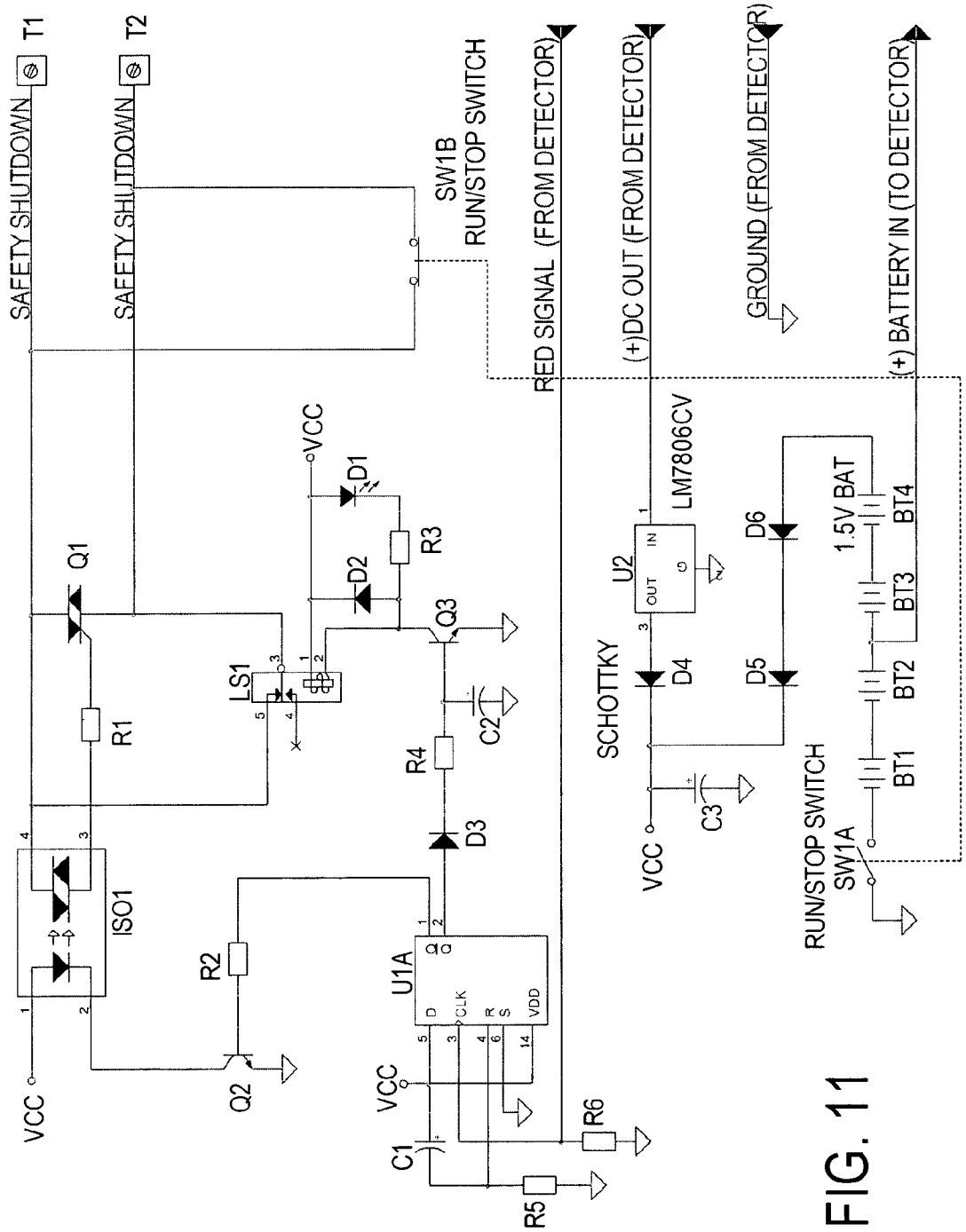
FIG. 11 is a representation using an electromechanical relay and active logic of an embodiment of the invention based on a 3V CO detector.

FIG. 11 is a representation of an embodiment of the invention using an electromechanical relay and active logic. This system was successfully interfaced to a commercial CO detector made by First Alert Model CO-605. This is one of the newest units in the market which plugs into the power mains and also has a battery backup using 2 AA type batteries, for a total of 3 Volts. Most of the CO detectors of this type in the market today use a 9 Volt battery. These 9 Volt batteries have a tendency to discharge faster than the AA or AAA types. An implementation to interface to a 9V battery backed up system is described below. It is also possible to implement the safety device by using a microcontroller with built-in (firmware) software. Referring to FIG. 11, batteries BT1, BT2, BT3, and BT4 are 1.5 Volt batteries. Switch SW1, being a DPDT type has two sections SW1A and SW1B. Batteries BT1 and BT2 are used to power up the backup section of the CO detector (total of 3 Volts) thru RUN/STOP switch SW1A (this is also the switch that will manually control the ignition and shutdown of the power generator). Note that when switch SW1A is OFF, power for the CO detector is interrupted. Therefore, there will be no drain to the batteries. Batteries BT1, BT2, BT3 and BT4 form a 6 volts supply to the electronics of the shutdown mechanism. Safety shutdown terminal T1 and safety shutdown terminal T2 are connected in parallel to the RUN/STOP switch of the power generator (switch 1010 in FIG. 10) as explained elsewhere. Switch 1010 is either disconnected and removed, or left in the ON position as explained above (so the engine can be run).

When the generator is not running, the CO detector unit will not receive power thru its main power terminals. Upon closure of SW1A, CO detector is energized. Most of the commercial detectors, upon insertion of the batteries (or in this case upon switching switch SW1A to ON position) the RED LED will briefly light up (alarm) as a self test. In order to avoid this blink to trigger the safety mechanism of embodiments of the invention, time constant given by C1 and R5 will hold "D" type flip-flop U1A on reset, and consequently negated output Qnot (Qnot means the logically inverted output of Q. If Q=H then Qnot=L, and if Q=L then Qnot=H. H means a logical HIGH and L means a logical LOW) of flip-flop U1A (pin 2 of U1A) will be in a high state, energizing relay LS1 thru diode D3, current limiting resistor R4, and buffer transistor Q3. This timing constant T=R5×C1 is long enough for the CO detector to finish the self test. Once relay LS1 is energized, electrical contact between terminals T1 and T2 will be open, as well as the electrical path thru SW1B (since switch SW1 is in the RUN position), effectively enabling to start the gas engine of the generator. Transistor Q2, current limiting resistor R2, optical isolator ISO1, triac Q1 and resistor R1 form an isolated redundant electronic relay, or solid state relay (SSR). Output Q of flip flop U1A (pin 1 of U1A) is low due to the reset issued as explained above. Q2 is then in a non conductive state, as well as light emitting diode of ISO1, therefore holding triac Q1 also in a non conductive state. The electrical path between T1 and T2 is therefore open. Note that terminals MT1 and MT2 of triac Q1 are electrically connected in parallel to the normally closed contacts of electromechanical relay LS1. Diode D2 protects transistor Q3 from damaging reverse voltage when coil of relay LS 1 is de-energized. LED D1 and resistor R3 indicates the status of the safety shutdown unit. If the LED is ON, the engine can be started. Clock input CLK to flip-flop U1A is low since RED LED indicator is OFF under normal operating circumstances. It is also weakly held down by pull-down resistor R6. Once the gas engine is started (manually, by means of a cranking battery or other electrically cranking, or by other means, depending on the type of power generator) the CO detector will receive main power (which could be 120 Volts or 220 volts) from the generator, and therefore the CO detector will revert to AC operation, conserving batteries.

The (+) DC OUT (i.e., the signal from power supply outputs 730 and 780 in FIG. 7 and FIG. 8) is now active, and reaches the input to linear regulator U2. Output of linear regulator U2 is around 6 volts, and after diode D4 will be around 5.7 volts (forward voltage of a schottky diode). This voltage is higher than the sum of battery voltages sum BT1, BT2, BT3 and BT4 (around 6 volts), less the voltage drop of around 1.4 volts thru series diodes D5 and D6. Since output voltage at the cathode of D4 (around 5.7 volts) is higher than voltage at cathode of D5 if no main voltage was present (around 4.6 volts), the safety circuit will be powered from the generator's main and not from batteries. At this point, the current drain from the batteries will be of that needed by the CO detector to check for a "low battery" condition. Capacitor C3 is used as additional DC filtering, and to clean up spikes.

If carbon monoxide raises to toxic levels in the environment, for any reason, the RED LED SIGNAL OUT of the detector will go high (caused by either a flashing LED or a constant ON RED LED signal, as explained in FIGS. 2, 3 and 4), causing output of flip flop U1A, Qnot, to go low, as well as Q output of flip-flop U1A to go high. As output Q of flip-flop U1A goes high, optoisolator ISO1 will conduct (LED energized by Q2) effectively putting the triac Q1 into conduction, and therefore shorting SAFETY SHUTDOWN terminals T1 and T2. At this point the engine will stop running. And flip-flop U1A output Qnot is now low. D3 is then no longer conducting, and transistor Q3 will stop conducting after time constant (dependent on R4 and C2) falls below approximately 0.7 Volts. This will then de-energize relay LS1, shorting also terminals T1 and T2, in parallel to already conducting triac Q1. This is done for one or more of the following reasons: (1)

Q1 will short terminals T1 and T2 earlier than the contacts of relay LS1 (which will short after a given time constant R4×C2) to preserve the relay's contact from arching and wearing out, and (2) for redundancy purposes, if Q1 fails in shutting down the engine, LS1 will do it.

Note that a low battery warning indication will cause the RED LED also to blink (this is normally done at a rate of one blip per minute) which will also cause the system to shutdown.

It is desirable that the safety shutdown system work even in the absence of power generated by the alternator's generator. If for some unusual reason the alternator goes bad (for example by an internal short of the windings) or because of a tripped fuse, or a cut wire, then the safety detection unit will continue to monitor for the presence of CO, and it will shut down the gas engine as a safety precaution if the batteries are low or there is no power received from the generator. On the same principle, if the batteries are removed by the user, and the same failure occurs (the generator will stop generating power) the system will immediately shut down due to the lack of power to hold relay LS1 with the contacts open. The same mechanism applies when the TEST/RESET button is actuated in the CO detector. An alarm status will be issued, triggering exactly the same mechanism as explained above. Since this system is intended to save lives, redundancy and possible scenarios knows to the inventor were considered.

When the system is running normally, with good batteries and with the generator generating power, by switching RUN/STOP switch SW1 to STOP or OFF position, power will be interrupted to the safety system, but before relay LS1 is de-energized (due to residual power in the system) switch SW1B (which is mechanically actuated simultaneously to SW1A) will short circuit terminals T1 and T2 effectively shutting down the gas engine further preserving the contacts of relay LS1. It is also important to understand that without batteries, the power generator will not be able to be started up. This is also a safety design consideration. If the power generator was allowed to be started in the absence of power, and the alternator went bad, the CO detector and safety unit will not be able to distinguish the difference between a non running generator trying to be started, or a running generator with a bad alternator, allowing the unit to be run even in the presence of dangerous levels of CO. Another embodiment of the invention includes a mechanically timed switch (described below) which will allow the engine to be started until power is generated. Using this type of switch, the CO detector will need not to have backup batteries, although the unit as described, with backup battery, is much safer. It is also important to understand that if the generator is shutdown by the safety system described herein, and switch SW1 is not turned off, the CO detector will audibly alerts the occupants that dangerous levels of CO caused the gas engine to be shut down. The unit will, indeed not only shut down but wake up the occupants to alert of a potentially lethal situation. In an embodiment with a mechanical timed switch, although the generator will be shut down and prevented from generating more CO, it may not alert the occupants of such a dangerous situation.

Figure 12:
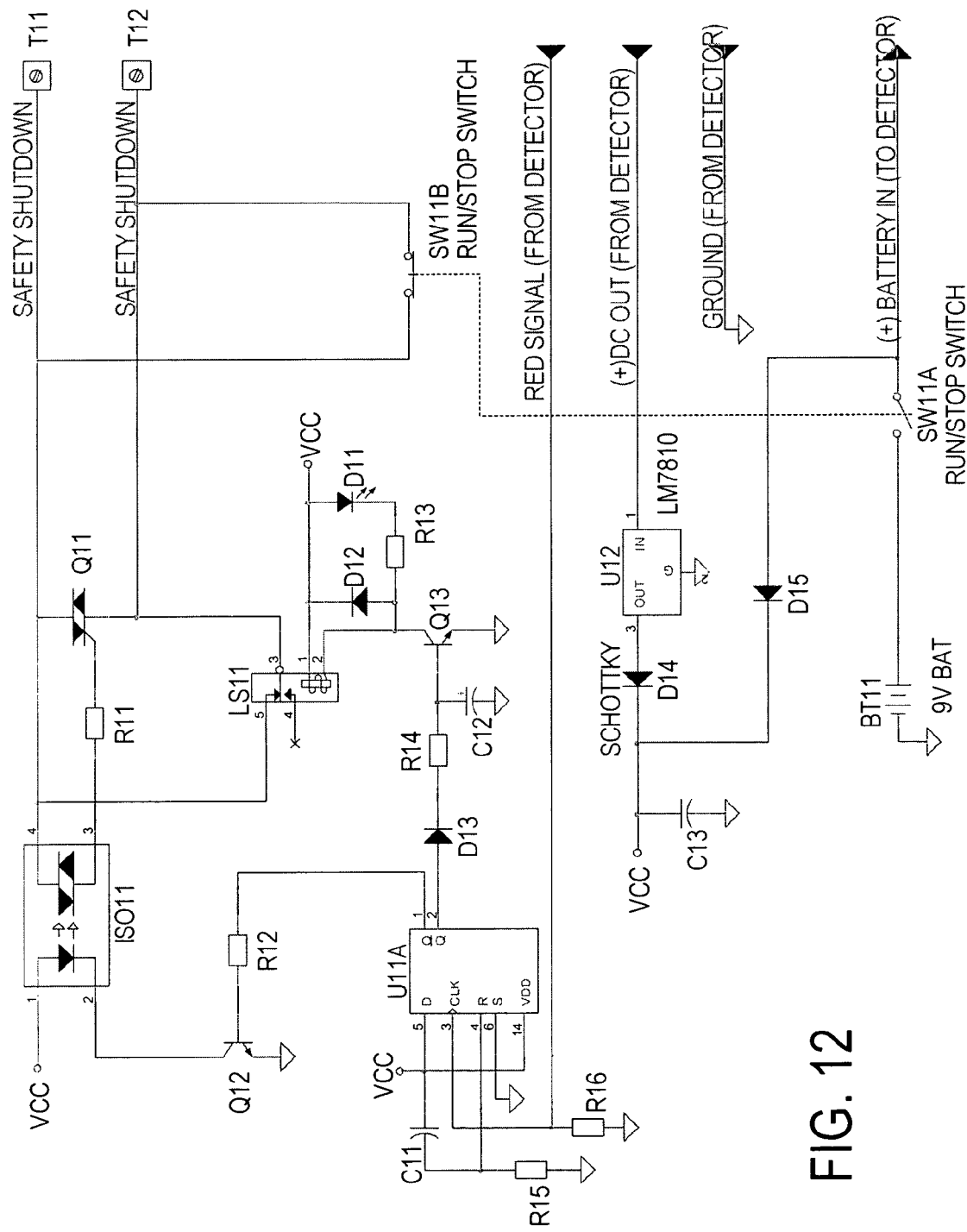
FIG. 12 is a representation using an electromechanical relay and active logic of an embodiment of the invention based on a 9V CO detector.

FIG. 12 shows a similar implementation, this time using a commercial CO detector with a 9 Volt battery. This is another representation of an embodiment of the invention using an electromechanical relay and active logic. This system was successfully interfaced to a commercial CO detector made by First Alert. As above, it is possible to implement the safety device using a microcontroller with built-in software (i.e. firmware). Referring to FIG. 12, switch SW11, being a DPDT type has two sections SW11A and SW11B. Battery BT11, is a 9 Volt battery used to power up the backup section of the CO detector thru RUN/STOP switch SW11A (this is also the switch that will manually control the ignition and shutdown of the power generator). Note that when switch SW11A is in the STOP or OFF position, power for the CO detector is also cut down. Therefore, there will be no drain to the battery. Battery BT11 also powers the electronics of the shutdown mechanism. Safety shutdown terminal T11 and safety shutdown terminal T12 are connected in parallel to the RUN/STOP switch of the power generator (switch 1010 in FIG. 10). Switch 1010 is either disconnected and removed, or left in the ON position as explained above (so the engine can be run).

When the generator is not running, the CO detector unit will not receive power thru its mains power terminals. Upon closure of SW11A, CO detector is energized. Most of the commercial detectors, upon insertion of the batteries (or in this case upon switching switch SW11A to ON) will briefly light up the RED LED (alarm) as a self test. In order to avoid this blink to trigger the safety mechanism embodiment of the invention, time constant given by C11 and R15 will hold "D" type flip-flop U11A on reset, and consequently negated output Qnot of U11A (pin 2) will be in a high state, energizing relay LS11 thru current limiting resistor R14, and buffer transistor Q13. This timing constant T=R15×C11 is long enough for the CO detector to finish the self test. Once relay LS11 is energized, electrical contact between terminals T11 and T12 will be open, as well as the electrical path thru SW11B (since switch SW11 is in the RUN position), effectively enabling to start the gas engine of the generator. Transistor Q12, optical isolator ISO11, triac Q11 and resistor R11 form an isolated redundant electronic relay, or solid state relay (SSR). Output Q of flip flop U11A (pin1) is low due to the reset issued as explained above. Q12 is then in a non conductive state, as well as light emitting diode of ISOM therefore holding triac Q11 also in a non conductive state. The electrical path between T11 and T12 is also open. Note that terminals MT1 and MT2 of triac Q11 are electrically connected in parallel to the normally closed contacts of electromechanical relay LS11. Diode D12 protects transistor Q13 from damaging reverse voltage when coil of relay LS11 is de-energized. LED D11 and resistor R13 indicates the status of the safety shutdown unit. If the LED is ON, the engine can be started. Clock input CLK to flip-flop U11A is held down by pull down resistor R16. Once the gas engine is started the CO detector will receive main power from the generator (which could be 120 volts or 220 volts) and therefore the CO detector will revert to AC operation.

The (+) DC OUT (i.e., signal from power supply output's 730 and 780 in FIG. 7 and FIG. 8) is now active, and reaches the input to linear regulator U12. Output of linear regulator U12 is around 10 volts, and after diode D14 will be around 9.7 volts. This voltage is higher than battery voltage BT11 (around 9 volts) less the voltage drop of around 0.7 volts thru series diode D15. Since output voltage at the cathode of D14 (around 9.7 volts) is higher than voltage at cathode of D15 if no mains voltage was present (around 8.3), the safety circuit will be powered from the generator's main and not from batteries. At this point, the only current drain from the batteries will be of that needed by the CO detector to check for a "low battery" condition. Capacitor C13 is used as additional DC filtering, and to clean up spikes.

If carbon monoxide concentration rises to toxic levels in the environment, for any reason, the RED LED SIGNAL OUT of the detector will go high (caused by either a flashing LED or a constant ON RED LED signal, as explained in FIGS. 2, 3 and 4), causing output of flip flop U11A, Qnot, to go low, as well as Q output of flip-flop U11A to go high. As output Q of flip-flop U11A goes high, optoisolator ISO11 will conduct (LED energized by Q12) effectively putting the triac Q11 into conduction, and therefore shorting SAFETY SHUTDOWN terminals T11 and T12. At this point the engine will stop running, and flip-flop U11A output Qnot is now low. D13 is then no longer conducting, and transistor Q13 will stop conducting after time constant given by R14 and C12 falls below approximately 0.7 Volts. This will then de-energized relay LS11, shorting also terminals T11 and T12, in parallel to already conducting triac Q11. This is done for two reasons: (1) Q11 will short terminals T11 and T12 earlier than the contacts of relay LS11 (which will short after a given time constant R14×C12) to preserve the relay's contact from arching and wearing out, and (2) for redundancy purposes, if Q11 fails in shutting down the engine, LS11 will do it. Note that a low battery will cause the RED LED also to blink (this is normally done at a rate of one blip per minute) which will also cause the system to shutdown. The same mechanism applies when the TEST/RESET button is actuated in the CO detector. An alarm status will be issued, triggering exactly the same mechanism as explained above.

When the system is running normally, with good batteries and with the generator generating power, by switching RUN/STOP switch SW11 to the OFF position, power will be interrupted to the safety system, but before relay LS11 is de-energized (due to residual power in the system) switch SW11B (which is mechanically actuated simultaneously to SW11A) will short circuit terminals T11 and T12 effectively shutting down the gas engine further preserving the contacts of relay LS11. It is also important to understand that without batteries, the power generator will not be able to be started up. This is also a safety design consideration. If the system was allowed to be started in the absence of power, and the alternator went bad, the CO detector and safety unit will not be able to distinguish the difference between a non running generator trying to be started, or a running generator with a bad alternator, allowing the unit to be run even in the presence of dangerous levels of CO.

Figure 13:
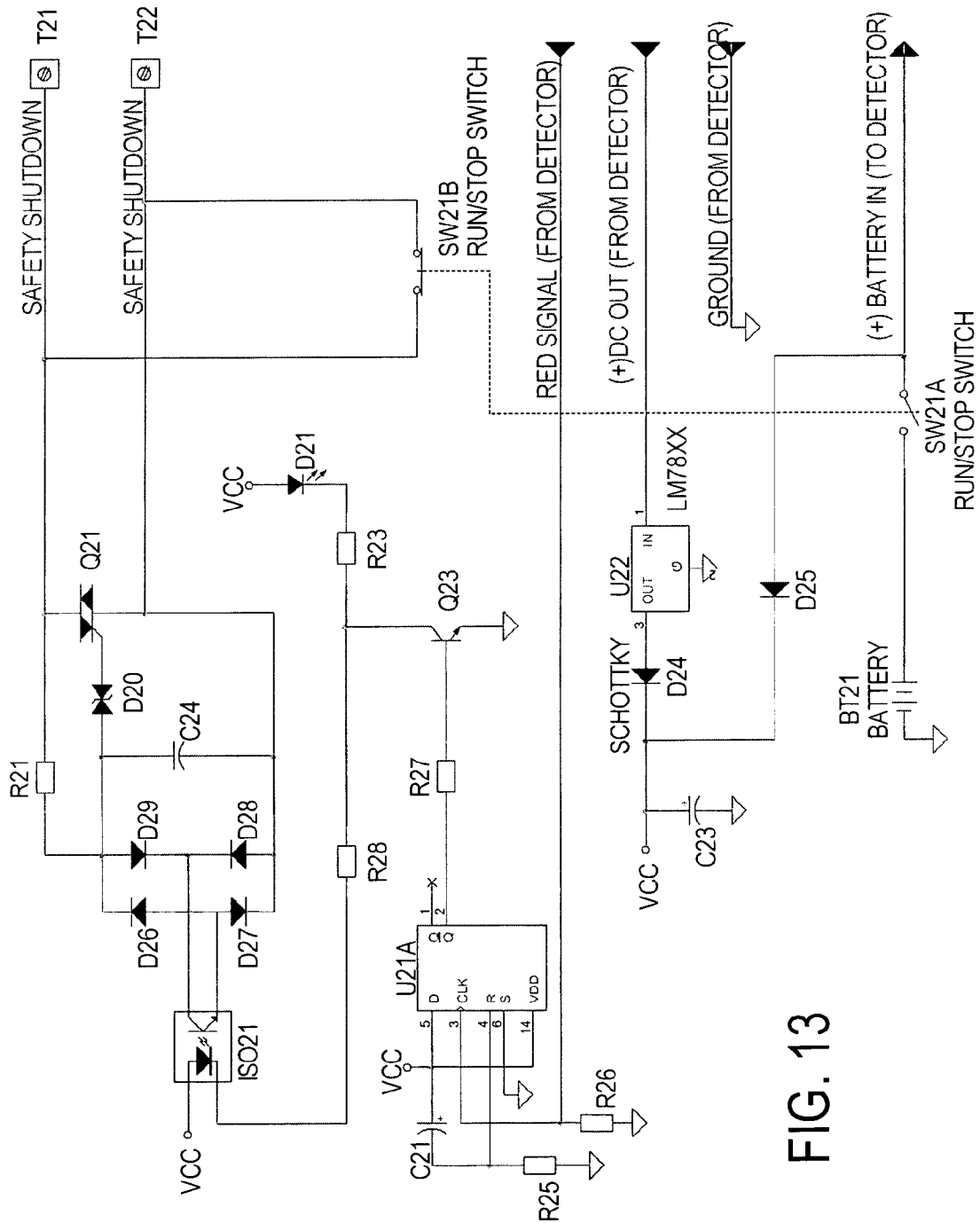
FIG. 13 shows an implementation, using a commercial CO detector with a solid state relay, using any type of battery.

FIG. 13 shows yet another embodiment of the invention which also uses a commercial CO detector but does not use an electromechanical relay, but rather an implementation of a normally closed solid state relay (SSR). This type of SSR will present a short on the terminals of the triac, for as long as there is no power applied to the circuit, therefore achieving exactly the same results of the "inversed logic" (i.e., "do not allow to start the engine until the safety unit is powered up and running"). This circuit can be used for any CO detector using any type of batteries (such as 9V or 1.5V or any combination of them). Since the electronic circuit operates exactly as described already in FIGS. 11 and 12, only the implementation of the normally closed SSR is explained below.

Referring to FIG. 13, U22 regulator LM78XX is chosen to regulate output voltage to around 2 Volts over the battery's BT21 voltage used in the detector. For example, if the detector uses two 1.5V batteries for a total of 3V, the regulator will be for 5 Volts. In such a case, a LM7805 may be used. In this embodiment of the invention, and for simplicity reasons, we eliminated redundancy of the mechanical relay. Note that since a normally closed solid state relay (NC SSR) is electronically implemented, the safety device will still disable the ignition of the engine even in absence of power (from the generator and/or battery BT21) to power the safety device and or the CO detector.

The combination of diodes D20, D26, D27, D28, D29, capacitor C24, triac Q21, and isolator ISO21 form an all solid state, optocoupled, normally closed switch circuit (or NC SSR). One portion of this static switch is a clamping device to turn off/eliminate gate drive and maintain very low power dissipation through the clamping component in addition to having low bypass leakage around the power triac device. In selecting the power triac for load requirements, gate sensitivity may be chosen to maintain low power requirements. Switch SW21, being a DPDT type has two sections SW21A and SW21B. Battery BT21, is used to power up the backup section of the CO detector thru RUN/STOP switch SW21A (this is also the switch that will manually control the ignition and shutdown of the power generator). Note that when switch SW21A is in the STOP or OFF position, power for the CO detector is also interrupted. Therefore, there will be no drain to the battery. Battery BT21 also powers the electronics of the shutdown mechanism. Safety shutdown terminal T21 and safety shutdown terminal T22 are connected in parallel to the RUN/STOP switch of the power generator (switch 1010 in FIG. 10). Switch 1010 is either disconnected and removed, or left in the ON position as explained above (so the engine can be run).

When the generator is not running, the CO detector unit will not receive power thru its mains power terminals. Upon closure of SW21A, CO detector is energized. Most of the commercial detectors, upon insertion of the batteries (or in this case upon switching switch SW21A to ON) will briefly light up the RED LED (alarm) as a self test. In order to avoid this blink to trigger the safety mechanism embodiment of the invention, time constant given by C21 and R25 (timing constant T=R25×C21 is long enough for the CO detector to finish the self test) will hold "D" type flip-flop U21A on reset, and consequently negated output Qnot of U21A (pin 2) will be in a high state, energizing optocoupler ISO21 which controls the NC SSR (formed by D20, D26, D27, D28, D29, C24, R21 and Q21 as explained above) via Q23 and R27.

Cathodes of D28 and D29 are then shorted thru ISO21 to the anodes of D26 and D27, which then causes Q21 to be open, and therefore SAFETY SHUTDOWN terminals T21 and T22 to be open, effectively allowing the gas powered engine of the generator to run. Note that T21 and T22 will be also open thru SW21B (since switch SW21 is in the RUN position). LED D21 and resistor R23 indicates the status of the safety shutdown unit. If the LED is ON, the engine can be started. Clock input CLK to flip-flop U21A is held down by pull down resistor R26. Once the gas engine is started the CO detector will receive main power from the generator (which could be 120 volts or 220 volts) and therefore the CO detector will revert to AC operation.

The (+) DC OUT (i.e., signal from power supply output's 730 and 780 in FIG. 7 and FIG. 8) is now active, and reaches the input to linear regulator U22. Output of linear regulator U22 is higher than battery voltage BT21 since we have chosen U22 for that reason. Since output voltage at the cathode of D24 is higher than voltage at cathode of D25 if no mains voltage was present, the safety circuit will be powered from the generator's main and not from batteries. At this point, the only current drain from the batteries will be of that needed by the CO detector to check for a "low battery" condition. Capacitor C23 is used as additional DC filtering, and to clean up spikes.

If toxic CO levels cause to trigger the CO detector, or power is removed to the detector whether due to its main supply being interrupted, or by removal of the CO detector's battery(ies), U21A's Qnot output will go low. Q23 will then be in a non conductive state, turning OFF internal LED of ISO21 causing its internal NPN output transistor to go into an open state. Bridge rectifier formed by diodes D26, D27, D28, and D29 will then cause triac Q21 to go into conduction mode effectively shorting SAFETY SHUTDOWN terminals T21 and T22, causing the gas engine to shutdown. This is one implementation of a normally closed SSR, and there are many other obvious to persons skilled in the art.

Figure 14:
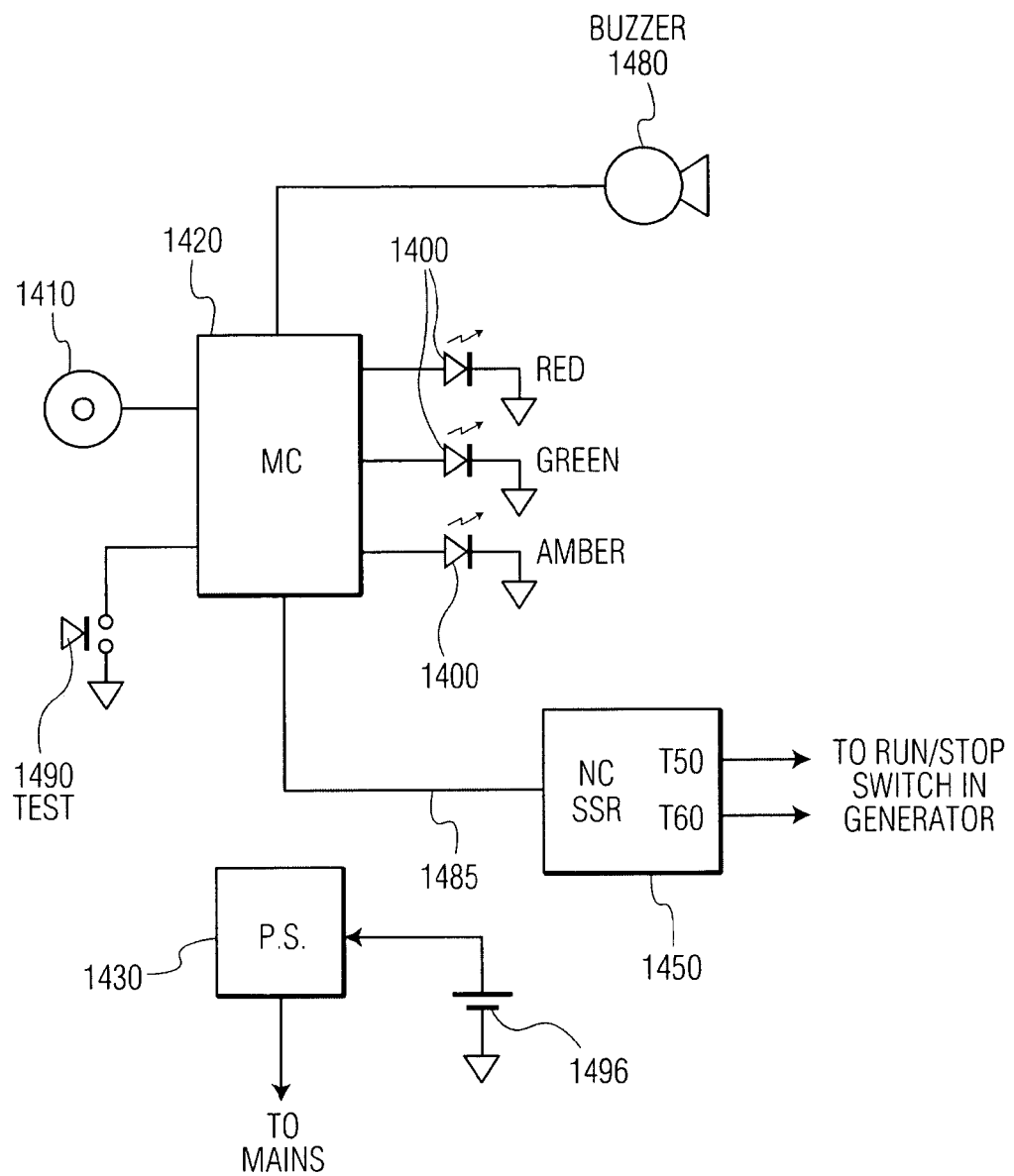
FIG. 14 shows an implementation using the microcontroller built inside a commercial CO detector.

FIG. 14 shows yet another implementation using the already-existing micro processor (microcontroller) built in and running the above-explained commercial type CO detector and alarm unit. For this example, a normally closed solid state relay (NC SSR) is used, as explained for the circuit in FIG. 13, for example. Note that this could also be replaced by a normally closed electromechanical type relay. In this implementation, and taking advantage of the microcontroller, the manufacturer of the CO alarm or detector will only need to include the electronics (or electromechanical relay) of a NC SSR and a software code routine may be combined to implement of a "D" type flip-flop similar to the hardware implementation and function of U1A in FIG. 11 with necessary delay upon power up or insertion of backup batteries in order not to trigger the SSR. Microcontroller 1420 polls the CO sensor 1410, and upon determination of dangerous levels of CO (based on algorithms such as the one taught in U.S. Pat. No. 7,142,105, incorporated by reference) it will accordingly indicate RED, GREEN, and AMBER LEDs 1400 (or at least one LED) with similar status indication as explained in FIGS. 2-4, as well as audible alarm or buzzer 1480. Output port 1485 from microcontroller 1420 is used as a control signal for NC SSR (or electromechanical relay) 1450. If control signal 1485 is high, then SAFETY SHUTDOWN TERMINALS T50 and T60 will be on an electrically open state. Once these terminals are connected in parallel to RUN/STOP switch of power generator as described herein (e.g. FIG. 16) they will control the gas engine of power generator 1600. If dangerous levels of CO are detected, or TEST switch 1490 of CO detector is used to test the unit, or backup batteries 1496 are low or removed, or power supply 1430 looses power due to a faulty generator, or any combination of these situations, will cause microcontroller 1420 to take output pin 1485 low, causing the NC SSR 1450 to go into a normally closed state, shutting down the gas engine.

Note that complete loss of power by a faulty alternator and removal of backup batteries, or tampering with the unit, to embodiments of the invention, will cause the NC SSR to shutdown the engine. Power supply 1430 and backup battery 1496 power the electronics of the CO detector.

FIG. 15 shows yet another implementation in which a commercial CO detector without a battery backup may be used and without compromising the safety logic described herein. Since a safety mechanism using a normally closed relay (weather electromechanical or electronic as in the case of a SSR) in absence of power will keep the generator in a STOP state, preventing it from being started, a temporary means is needed to allow the generator to be started up, until it starts generating enough power to power up the electronics of the safety device and CO detector, and then maintain the electromechanical relay or SSR in an energized state, thus allowing the gas engine to be run or kept running. Safety device 1500 comprising a CO detector and associated safety interrupt circuitry as explained in different implementations above, is connected and powered by power outlet 1550 in power generator 1540. Contact 1520 of electromechanical relay. 1510 (can be also a NC SSR) is a normally closed contact. When the coil of relay 1510 is not energized, contact 1520 is shorted. Manual switch 1530 is a normally closed momentary OFF electromechanical pushbutton switch; on its simplest implementation, this switch is electrically open for as long as the pushbutton is depressed.

When the gas powered generator is not running, then there is no power supplied to safety device 1500, and therefore there is no power to energize relay 1510, causing electrical path between T30 and T40 to be shorted. Since SAFETY SHUTDOWN terminals T30 and T40 are connected in parallel to RUN/STOP switch 1560 of gas powered generator 1540, the generator cannot be started. In order to start the generator, momentary OFF switch 1530 needs to be depressed by hand and then the engine started. Once the engine has been started, generator 1540 will power safety device's circuitry 1500 (thru power outlet 1550), which in turn, and under normal operating conditions, will energize relay 1510; relay's contact 1520 will then be open due to relay 1510 being energized, interrupting the electrical path between terminals T30 and T40 and allowing the gas engine to continue running. At this point, and once the engine has started, manual pushbutton 1530 needs not to be depressed any longer. If toxic levels of CO are detected, safety device 1500 will de-energize relay 1510 as explained in other implementations of the safety device; the relay's switch 1520 will now be shorted, shorting terminals T30 and T40 (thru normally closed manual switch 1530) which in turn will shutdown the gas engine. Similarly, if TEST button 1580 in the CO detector is depressed, a gas engine's shutdown will be accomplished. TEST button 1580 (on internal CO detector) mimics a high level of CO. TEST button 1580 will now be used as the STOP button to shut down the engine. Each time the engine will be shut down thru the TEST button, the safety device will also be tested.

In another scenario, if generator's alternator fails for any reason, regardless of the CO concentration present on the ambient, power to safety device 1500 will be interrupted, de-energizing relay 1510 and repeating the gas engine's shutdown as explained above. This is yet another safety net in case that the power to the safety device is interrupted, disabling the safety interrupt device and CO detector.

Another embodiment may include a "timed" mechanical switch, similar to those used in hot tubs, or attic fans. This switch 1530 once pushed (or rotated, depending on the type chosen) will momentary open the electrical path for a fixed amount of time, say for example 15 seconds. Within this time window, the engine can then be started. Upon the expiration of this mechanical timer, in this example 15 seconds, the switch will return to its normally shorted position. This will free the user both hands to start up the gas engine. If more time is needed after the initial mechanical timeout expired, an additional actuation of the timed switch will give an extra 15 seconds.

Figure 16:
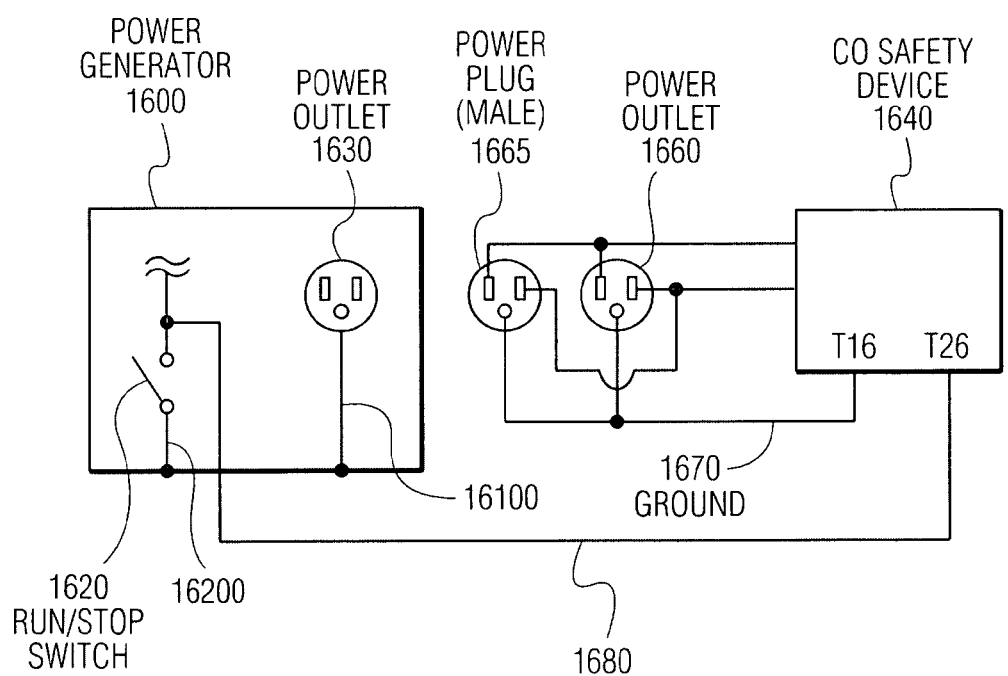
FIG. 16 shows a block diagram of an overall interface to a new or retrofitted portable power generator.

FIG. 16 is a block diagram showing the way to connect embodiments of the invention to a generator, such as within a new power generator, or for a retrofit kit for existing power generators. Gas powered generator 1600 may be any type, including battery start (battery crank up type) or manual start ("pull rope" type). Power outlet 1630 supplies power from power generator 1600. RUN/STOP switch 1620 is the switch that enables to start the gas engine or shuts down the gas engine (if it was running). One way that this switch may be internally connected is one lead 16200 connected to metal frame of generator 1600 which is also electrically connected to the ground of the alternator and ground 16100 of power outlet 1630. Safety device 1640 receives power from generator thru power plug 1665 once plugged into generator's power outlet 1630. Power outlet 1660 is wired in parallel to power plug 1665 thru a proper wire gage to support the maximum current supplied by the generator 1600. Appliances that were previously plugged into generator's power outlet 1630 will now be plugged into power outlet 1660. SAFETY SHUTDOWN signal T16 is wired to ground pins of power plug 1665 and power outlet 1460; signal T26 1680 is the only electrical connection that may be made to the generator in addition to plugging in power plug 1665 to power outlet 1630. In all commercial generators, this is a readily and accessible wire (normally yellow or black in color), and quick connect solder less terminals can be used to effectively make this electrical connection, shown as 1680. If the safety system shuts down due to a detected toxic level of CO, or low backup batteries, or any other reason as explained herein, SAFETY SHUTDOWN terminals T16 and T26 will be shorted, effectively shutting down the gas engine.

Existing commercial generators also may have a "low oil" normally open switch attached to the oil pan of the gas engine. This is another point of connection that may be effectively used to shut down the gas engine. This wire is typically black or yellow in color in most of the power generators, and it is also easily accessible, since the oil pan is always visible at the bottom of the power generator's frame.

Figure 17:
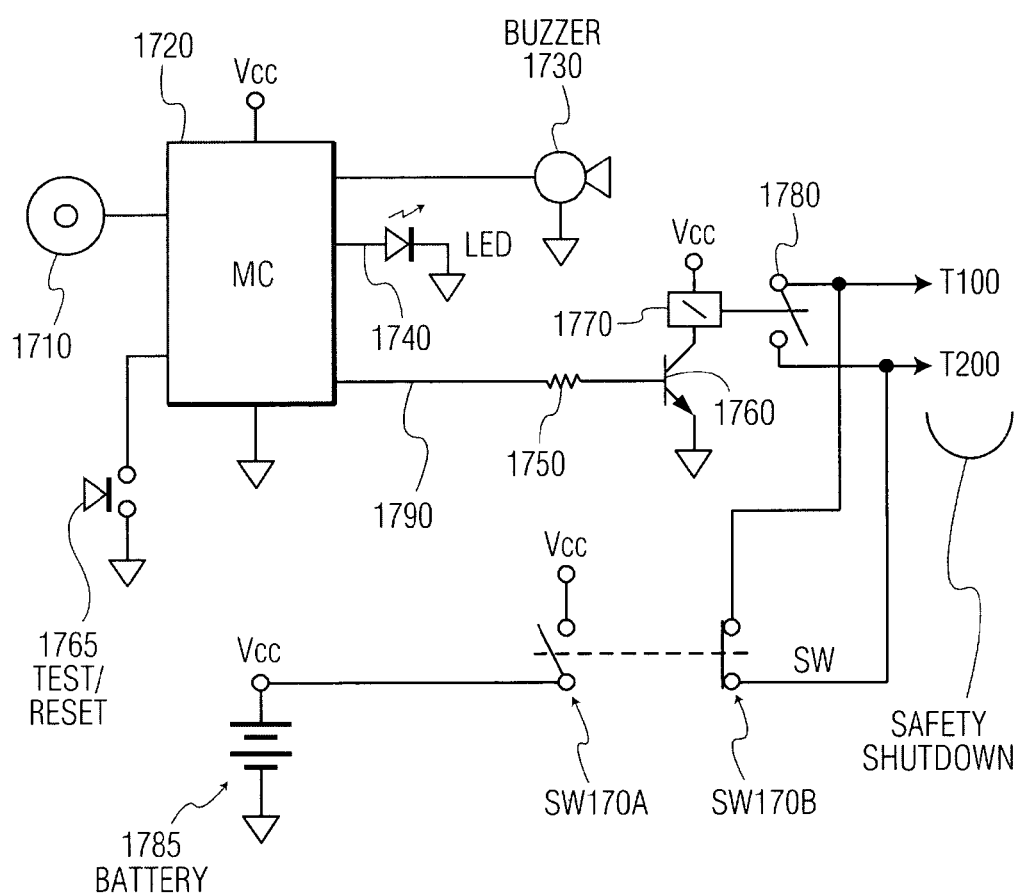
FIG. 17 shows a basic implementation of an embodiment of the invention by using a simple commercial CO detector.

FIG. 17 shows one implementation of an embodiment of the invention by using the simplest commercial available CO detector in the market. A safety device of this type may use this CO detector or it may be manufactured as a whole unit. The possible advantages of this type of safety device are:

(a) It may not need to be powered by the generator, making its installation in new portable power generators or retrofit of existing generators easier.

(b) Lower manufacturing cost, by eliminating extra components, such as transformers, diodes, filtering capacitors, and additional electronic components.

(c) Small physical size due to the elimination of additional components, some of them big in size, such as the magnetic transformer used in the mains power supply.

(d) A large amount of basic CO detectors exist in the commercial market.

Possible disadvantages are:

(e) If the CO detector fails, it may not shut down the engine in cases of the presence of toxic levels of CO.

(f) It may be possible to start the engine even if the CO detector is faulty.

(g) Since the CO detector (or detection unit if the safety device is manufactured as a whole system instead of using a commercial CO detector) needs batteries to function, the removal of the batteries may totally disable the safety shutdown system allowing the power generator to run even in the presence of toxic levels of CO (h) If the batteries used to power the safety device are bad or very low, the safety device may also be disabled, again, allowing the power generator to be run in any condition.

Referring to FIG. 17, switch SW170, being a DPDT type has two sections SW170A and SW170B; it will manually control the ignition and shutdown of the power generator. Battery 1785, is used to power up the CO detector and safety device thru normally open RUN/STOP switch SW170A. Note that when switch SW170A is in the STOP or OFF position, power for the CO detector is interrupted. Therefore, there will be no drain to the battery 1785. Safety shutdown terminal T100 and safety shutdown terminal T200 are connected in parallel to the RUN/STOP switch of the power generator, for example, of switch 1010 in FIG. 10. Switch 1010 is either disconnected and removed, or left in the ON position as explained above (so the engine can be run). Normally Closed switch SW170B is also connected in parallel to terminals T100 and T200. When SW170B is in the RUN mode (SW170A will then be electrically closed), terminals T100 and T200 will also be electrically open, allowing the generator to run. When switch SW170B is switched to the STOP position (SW170A will now interrupt power to safety device and CO detector), it will short terminals T100 and T200 effectively shutting down the engine. Microcontroller 1720 polls the CO sensor 1710, and upon determination of dangerous levels of CO (based on algorithms such as the one taught in U.S. Pat. No. 7,142,105) it will accordingly indicate CO level and battery status. RED LED 1740 with similar status indication as explained in FIG. 2, as well as audible alarm or buzzer 1730. Output port 1790 from microcontroller 1720 is used as a control signal to actuate a normally open (NO) electromechanical relay (or NO SSR) 1770. Note that a NO type relay is used in order to conserve the life of the battery. In normal operating conditions, and in the absence of toxic levels of CO, control signal 1790 is low. Since NO relay 1770 is de-energized, SAFETY SHUTDOWN TERMINALS T100 and T200 are on an electrically open state. Since these terminals are connected in parallel to RUN/STOP switch of power generator as described elsewhere herein (i.e. FIG. 16) they will control the gas engine of power generator 1600. If dangerous levels of CO are detected, or TEST/RESET pushbutton 1765 is used to test the unit, microcontroller 1720 under software control, in addition to setting LED 1740 and sounding audible alarm 1730, will set output pin 1790 high. This will cause buffer transistor 1760 thru base current limiting resistor 1750 to go into saturation, causing NO relay 1770 to be energized. Once energized, relay contacts 1780 will present a short in SAFETY SHUTDOWN terminals T100 and T200; this electrical short will, in fact, shutdown the engine. Alarm indicator LED 1740, audible buzzer 1730, and relay 1770 can be returned to their normal operating condition either by depressing TEST/RESET pushbutton 1765 or by switching off power to the safety device thru RUN/STOP switch SW170. Once the system is returned to the normal non-alarm state (and by properly ventilating the area in case that the system detected high levels of CO), the gas engine will then be enabled to be started again.

TEST/RESET pushbutton 1765 has a double function, as in some of the commercial CO alarm units. If the safety device is in a non-alarm mode (no dangerous levels of CO detected) by depressing TEST/RESET pushbutton will cause microcontroller 1720 to simulate an alarm, and go into an alarm mode, and as explained above, it will also shutdown the gas engine. If the safety device was in an alarm state, depressing TEST/RESET pushbutton will disable the audible alarm, but it will not de-energize NO relay 1170, keeping the gas generator in a stopped mode. It is possible that the only way that relay 1770 may be de-energized is by ventilating the area, and letting microcontroller 1720 go into a non-alarm mode (by measuring and detecting a safe level of CO). The additional software functions used to actuate the relay as explained here are minor software additions to the existing software running microcontroller 1720, are as discussed above and incorporation the algorithms taught in U.S. Pat. No. 7,142,105 (incorporated by reference). Note that electromechanical relay 1770 and associated circuitry, such as 1750 and 1760 can be replaced by a solid state relay.

Figure 18:
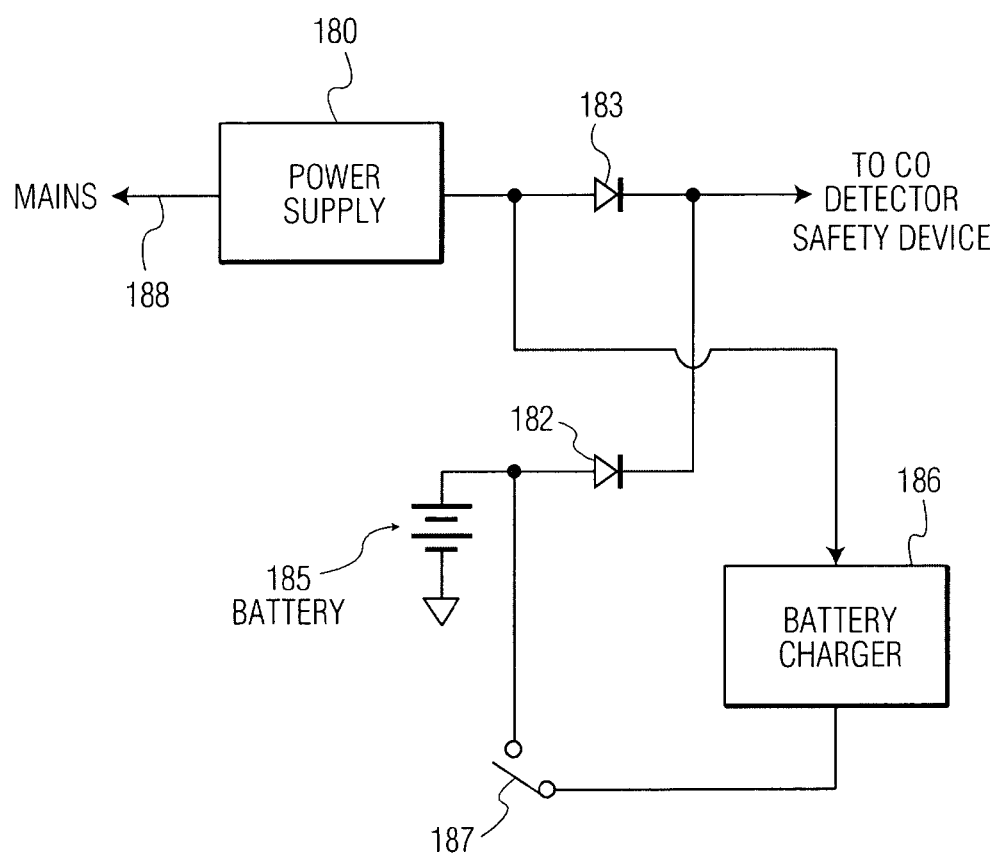
FIG. 18 shows a typical internal power supply of a CO detector used to recharge and in conjunction with rechargeable batteries.

FIG. 18 shows the block diagram of an internal power supply to power CO detector and safety device (whether is a commercial unit or an OEM type manufactured unit for use as a safety device as described herein); said power supply 180, in addition to power the safety device, it will be used to power up a battery charging circuitry 186. The safety device described here, which can be anyone of the embodiments described above, will then contain rechargeable batteries 185, according to the type of CO detector used (i.e. 1.5V or 9V or a combination) which will be used as explained herein. Furthermore, the safety device works most of the time using the power generated by the portable gas generator. Rechargeable batteries can be of the NiCd, NiMh, SLA (sealed lead acid) or any other suitable type of battery and circuitries known to those of skill in the art. Power supply 180, being part of the safety device and CO detector, is plugged into the power generator in a similar manner as explained with respect to FIG. 16. When the power generator is not running, and as explained above, RUN/STOP switch interrupts the power to the safety device, therefore there is no current drain from the backup batteries. Batteries will only discharge due to their internal resistance. Once the generator is started, safety device will obtain power from power supply 180, since the generator is generating power. Diode 183 will then be conducting, while diode 182 will be open, further isolating rechargeable battery(s) 185. Battery charging circuit 186 is used to charge batteries 185. CHARGE/NORMAL switch 187 is left in the closed position when rechargeable batteries are used in the system. This switch is used to disable the battery charging circuitry if the rechargeable battery does not have enough power to allow the cranking of the power generator. If this was the case, for example after a long year where the power generator was not used, by simply moving the switch to the NORMAL position, regular alkaline or other type of non rechargeable batteries could be used.

Figure 19:
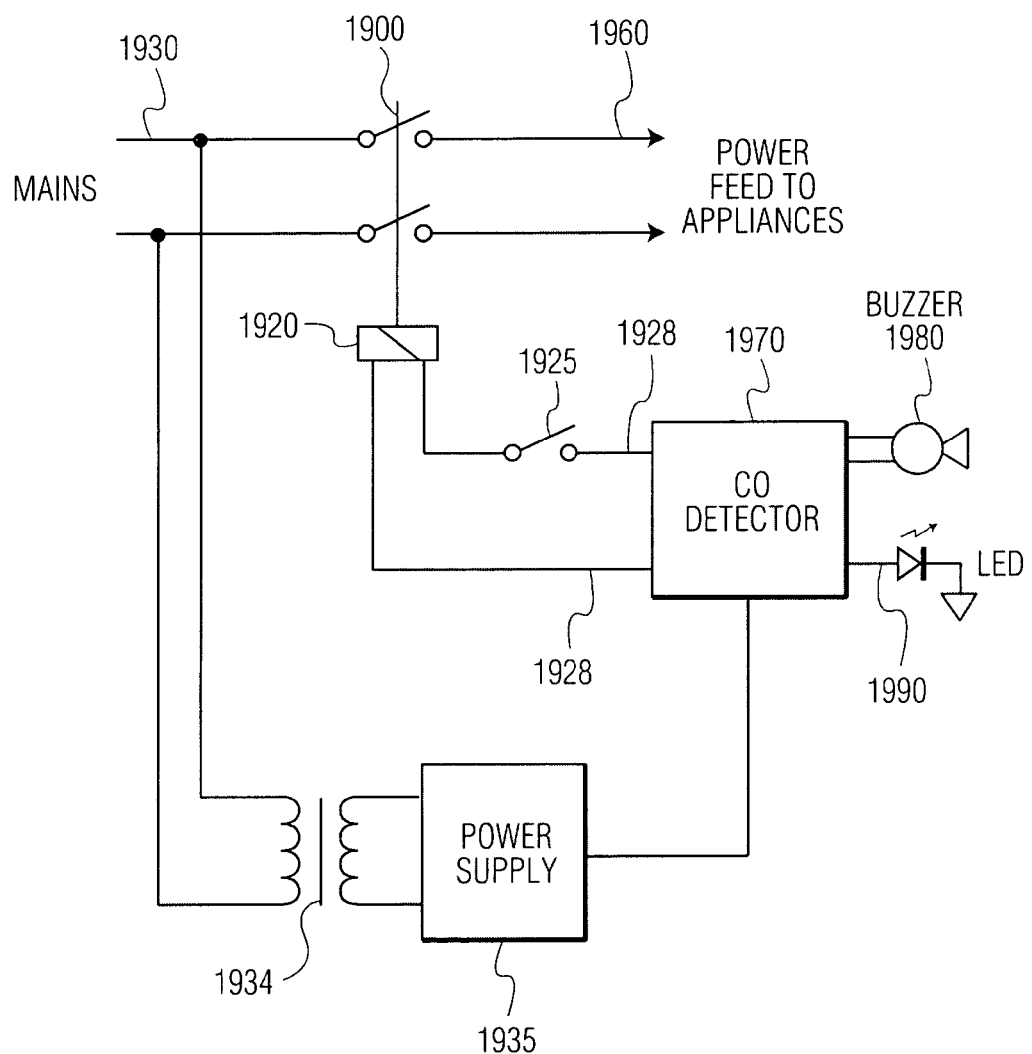
FIG. 19 shows an implantation of a power switch which interrupts power to the room or appliance when toxic gas is detected.

FIG. 19 shows an implementation of a power switch, which may be manufactured as a retrofit or replacement switch for regular wall switches, and it will shut down the power to the appliance that is wired to that switch in case toxic levels of gas (such as CO) is detected.

This switch can be used, for example, to replace the commonly used switch denoted as "EMERGENCY" in gas and oil fired furnaces. This switch is usually mandatory by the NEC (National Electrical Code) for installations of all furnaces. Embodiments of the invention may be built in such a way that they may fit in commonly used electrical boxes as a replacement switch, both for existing and new constructions. Incoming power from main 1930 is wired to normally open relay contacts 1900 of electromechanical relay 1920 (note that this electromechanical switch could be a NO SSR). Main power continuously feeds power to transformer 1934 regardless of relay's contacts 1900 being opened or closed. This guarantees that the CO detector and associated safety circuitry are powered all the time. Transformer 1934 and power supply 1935 power the electronics and safety device. Toxic gas detector, or CO detector 1970 could be any commercial CO detector of any type as described above. LED 1990 is a visual indicator or a plurality of LED's to indicate status of CO detector 1970 according to FIGS. 2-4. Buzzer or audible indicator 1980 sounds in the event of a detection of toxic levels of the gas being monitored. Control lines 1928 energize or de-energize coil of electromechanical relay 1920 in response to alarms or normal operation, functioning on a similar way to the embodiments described above. Switch 1925 is used as a manual switch to turn the power feed to appliances ON or OFF in a similar way as the mechanical switch being replaced.

In normal operation, and in the absence of toxic levels of gas, relay 1920 is continuously energized (provided manual ON/OFF switch 1925 is electrically closed) thru control lines 1928 from CO detector receiving power from power supply 1935. Contacts 1900 of electromechanical relay 1920 are therefore electrically closed, providing power to the appliance thru power feed 1960 (for example a gas or oil fired furnace in a residence). If high levels of toxic gas are detected, or the CO detector's alarm 1970 is triggered thru the TEST switch, relay 1920 will be de-energized, effectively and immediately removing power from the appliance connected to power feed 1960. Electromechanical relay 1920 will again be energized (and power restored to the appliance) only when CO detector 1970 detects that levels of the toxic gas being monitored have returned to safe levels.

In normal operation conditions, manual switch 1925 will remove power to relay 1920, effectively shutting down power to the appliance, acting as a normal ON/OFF switch.

In the embodiments described above, safety device gets the main power from the generator's outlet. In certain generators, where the safety device will be built-in, the main power may be obtained directly anywhere within the generator itself, or by internal wiring in the control panel.

In addition, it is possible to use the low voltage from the magneto of a gas-engine, or for example, if another coil somewhere is wrapped in the U-shaped armature, to obtain the main power for the safety device to operate and/or preserve the backup batteries. It is also important to point out that many commercial generators generate 12 Volts DC, which can be also effectively used in any of the embodiments described, to power up the safety interrupt electronics as well as the CO detector. Such a generator is manufactured by Champion model C46535.

Figure 20:
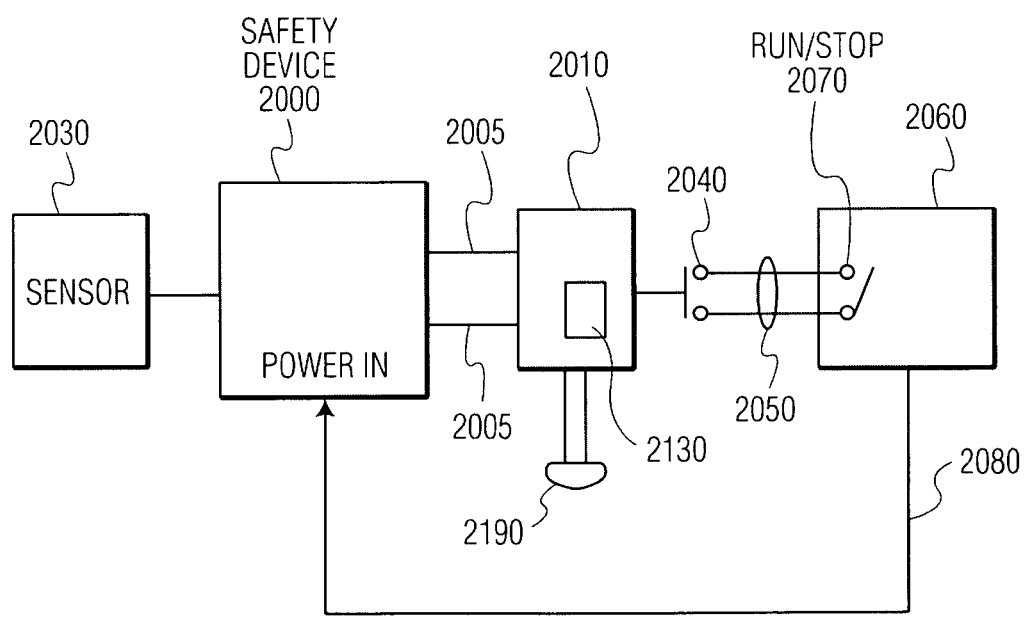
FIG. 20 shows an implementation with a commercial CO detector without a battery backup and with a special electromechanical switch.

FIG. 20 shows an embodiment of the invention, using an electromechanical switch without the need for a dedicated NC relay or SSR as in the rest of the implementations. This may be the most economical solution, and it may not need the use of backup batteries for the safety device. In essence, this is a mechanical implementation of an electronic SET/RESET type flip-flop, where the SET function is performed manually by pushing a button, and the RESET is performed by a solenoid when the solenoid gets de-energized.

A possible disadvantage of this type of system is the fact that in order to trip the switch and effectively shut down the generator, the safety device needs to have power at least once to energize the holding solenoid. If the alternator in the power generator is defective, and it never generates power once it is started, the gas engine may continue to generate toxic fumes which may reach dangerous levels. If there is no power altogether, the CO detection system will not be able to detect the levels of the toxic fumes and shut down the engine, in which case a safety device with battery backup may be desirable. Safety device 2000 analyzes the level of toxic gas in the air, by using sensor 2030. Mechanical button 2190 of electromechanical switch 2010 is pushed manually in order to start the engine. Once this button is pushed in, contacts 2040 of switch 2010, connected in parallel thru connection 2050 to generator's RUN/STOP switch 2070, are mechanically and electrically kept in a normally open state, allowing power generator 2060 to be run (since RUN/STOP generator's switch 2070 is open or absent, as explained herein). Once power generator 2060 is running, power generated by the alternator (or ignition system), is then used to power up safety device 2000. Once powered up, safety device 2000 energizes and keeps energized internal solenoid 2090 of electromechanical switch 2010. The normal state of safety device 2010 is to have solenoid 2090 energized. That is, if levels of toxic gases are safe, solenoid 2130 is kept energized.

Once levels of toxic gases reach dangerous levels, solenoid 2130 is de-energized, tripping electromechanical switch 2010, which in turn will short normally closed contacts 2040, effectively shutting down the power generator 2060. Note that if for any reason the power generator stops generating power, safety device 2000 will lose power, and in turn, solenoid 2090 be de-energized, again, effectively shutting down the generator, in this case for redundant and safety reasons. Note that all electronic circuits used in the other embodiments described above will work with this mechanism, in place of the NC electromechanical relay or NC SSR.

Figure 21:
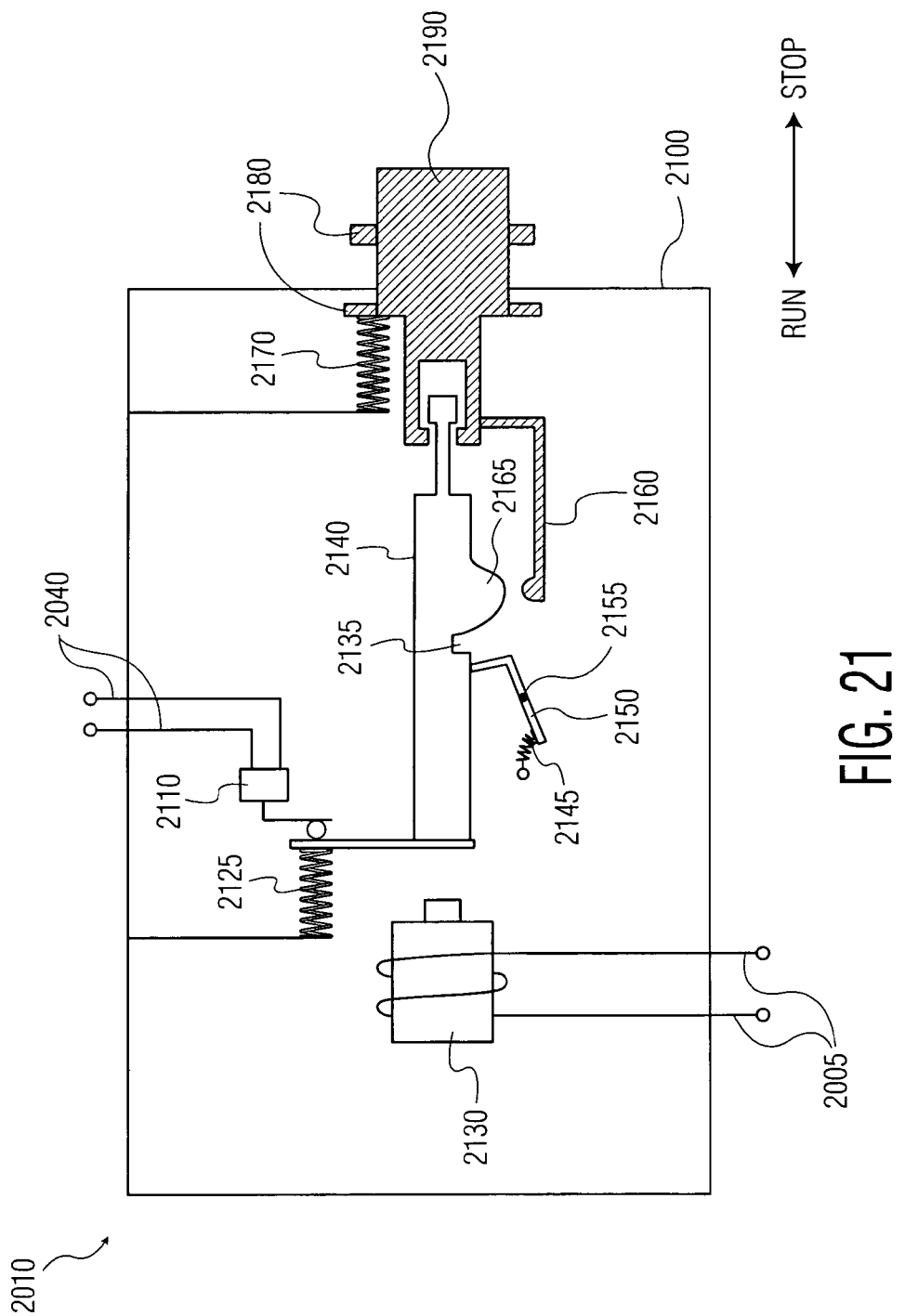
FIG. 21 shows an electromechanical switch to be used in conjunction with the safety device—in the STOP mode.

FIG. 21 shows one implementation of such electromechanical switch 2010 of FIG. 20, in the de-energized position (i.e., before the generator can be run—so power is absent). Note that this is one type of implementation, and persons skilled in the art may implement other types. Housing 2100 houses all the electromechanical components of the switch. Knob 2190 is used to RUN and or STOP the power generator. Spring 2170 returns knob 2190 to its resting position. Micro switch 2110 is a normally open switch (when not actuated its contacts 2040 are electrically open). As shown, micro switch 2110 is actuated, and therefore electrical connections 2040 present an electrical short. Spring 2125 returns plunger 2140 to its resting position when solenoid 2130 is not energized. Plunger 2140 has a projection 2165 and a notch 2135, and it is made of a magnetic material, which will cause its retraction when solenoid 2130 is energized. Lever 2150 can rest on either one of two stable states "A" or "B", due to compressed spring 2145 and pivoting point 2155. Shown in FIG. 21 is state "A", which keeps pressure against plunger 2140.

Figure 23:
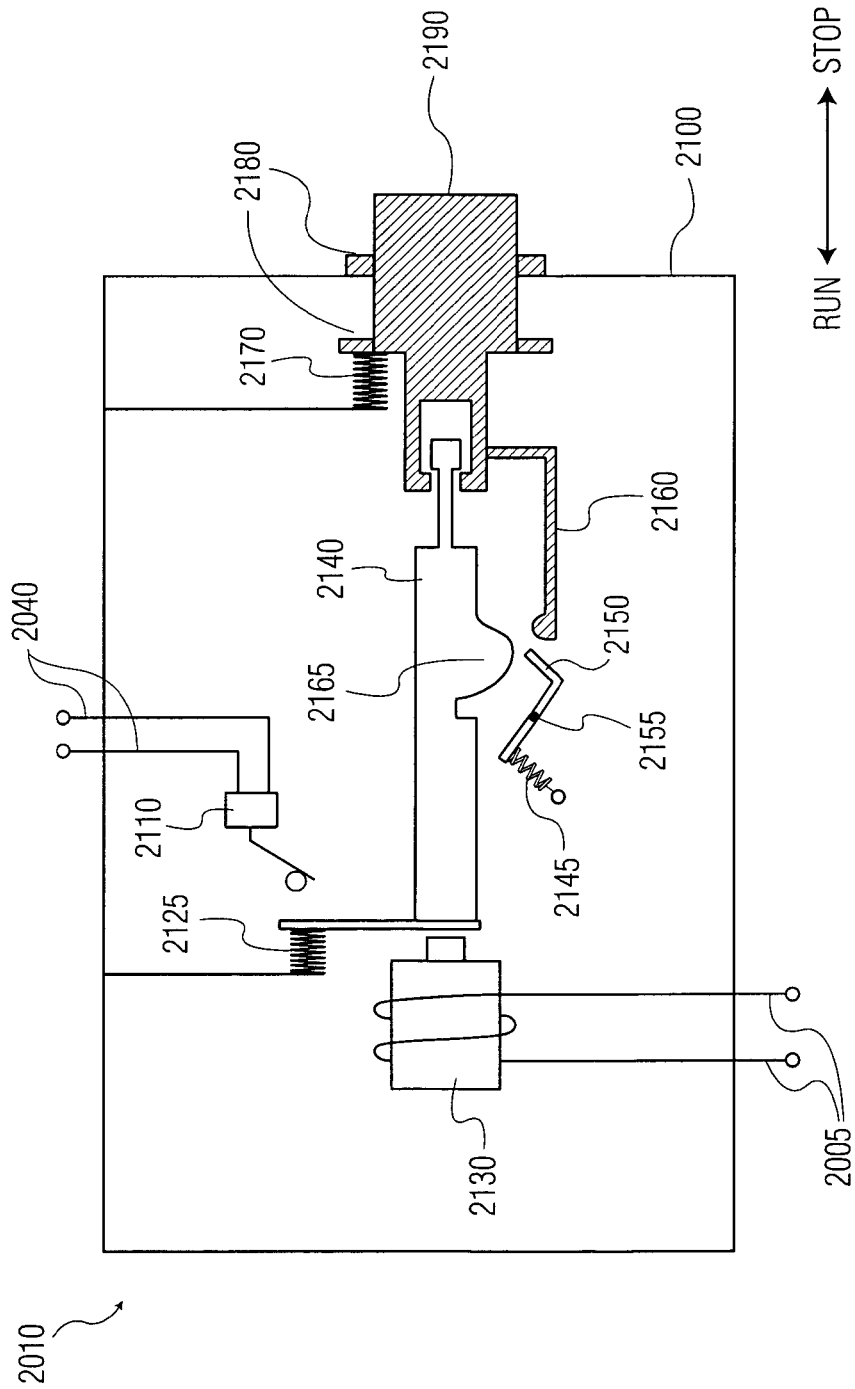
FIG. 23 shows the same electromechanical switch in the RUN position, with the generator running.

FIG. 23 shows lever 2150 on its stable "B" state. Spring 2145 is used to keep lever 2150 in either one of the two states. Extension rod 2160 of knob 2190 is used to return lever 2150 from state "B" to state "A" once knob 2190 is pushed in. Knob 2190 is kept in place by stops 2180, which also limits is travel distances.

Figure 22:
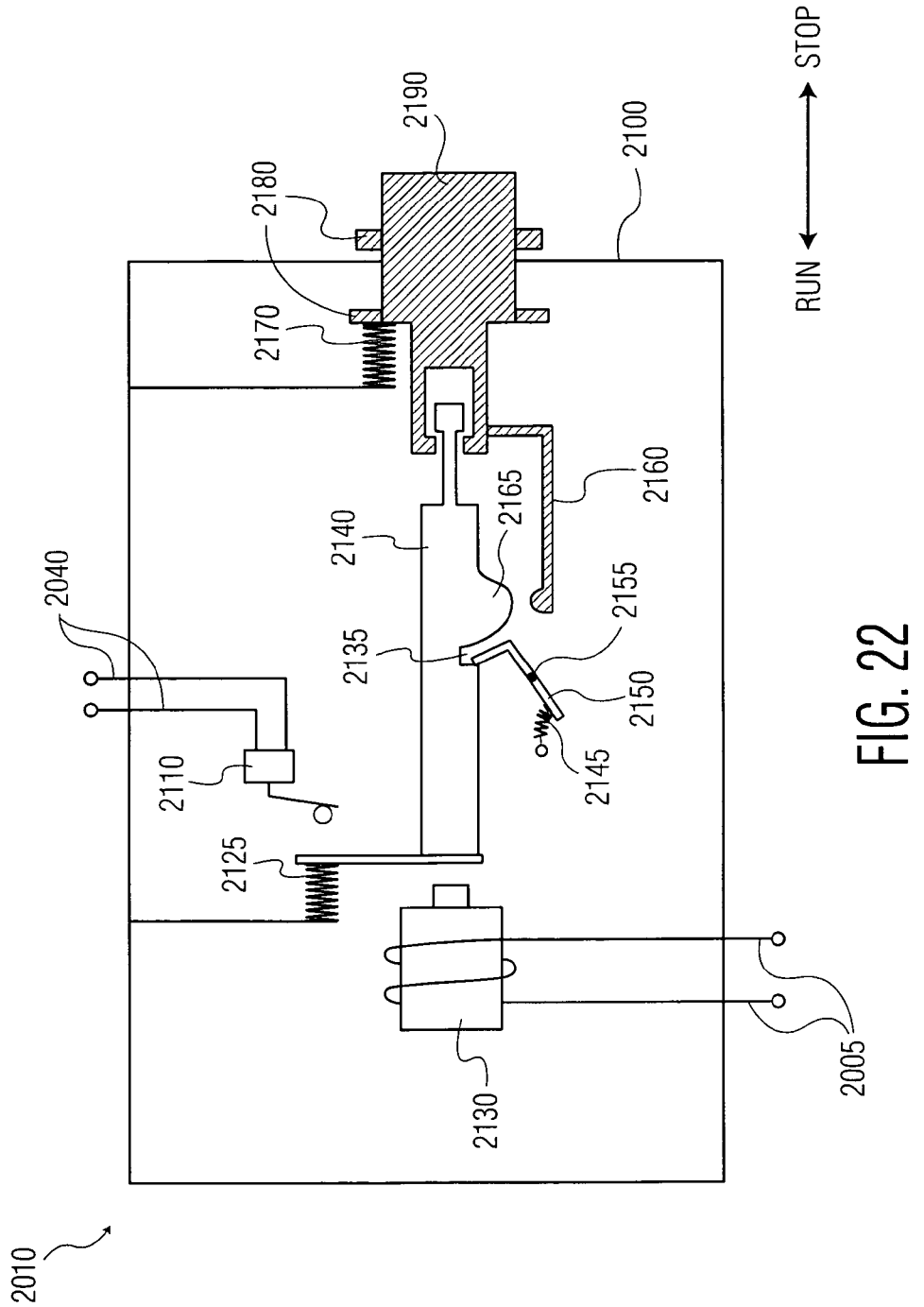
FIG. 22 shows the same electromechanical switch in the RUN position, prior to running the generator.

In order to start the generator, knob 2190 is pushed in (towards the housing), causing spring 2170 to compress; it also pushes plunger 2140, compressing also spring 2125. Once notch 2135 of plunger 2140 lines up with lever 2150 (and due to pressure caused by spring 2145 and pivoting point 2155), lever 2150 will hold plunger 2140 in place (as shown in FIG. 22). Spring 2125 is slightly compressed, and micro switch 2110 will now be electrically open, presenting an electrical opening on connections 2040.

FIG. 22 shows this state in detail (generator is ready to be started, but not started yet, and therefore safety device is not energized). Plunger 2140 is retained in position (after being manually pushed in by knob 2190) by lever 2150, which holds it mechanically locked because of spring 2145, and pushing lever 2150 around its pivoting point 2155 (in addition, lever 2150 "jams" plunger 2140 due to tension in springs 2125 and 2170). Plunger 2140 is now compressing spring 2125, and also releasing micro switch 2110, which in turn (since it is a normally OPEN switch) allows the generator to be started. Note that if lever 2150 was previously in state "B" (not ready to hold plunger 2140 in place thru notch 2135), by depressing knob 2190 to the RUN position, it will change lever 2150 to state "A" by means of push rod 2160. Now, the generator can be cranked up (manually or electrically). Once cranked up, the generator will now generate power.

FIG. 23 shows the state of the switch while the generator is running. Once the generator started to generate power (thru the alternator or ignition system), it will power safety device 2000, and therefore electromechanical switch 2010 as explained with respect to FIG. 20.

In this state, safety device 2000 energizes solenoid 2130 thru electrical connections 2005 when the safety device is not detecting high level of toxic gases. Due to its receiving power, solenoid 2130 pulls ferromagnetic plunger 2140, and projection 2165 pushes down lever 2150 to stable state "B." Stable state "B" is as shown in this figure. Lever 2150 is held in state "B" due to spring 2145 and pivoting point 2155 of lever. Spring 2125 was also further compressed. In this state, and because of lever 2150 being in state "B," de-energizing solenoid 2130 will cause (because of compressed spring 2125) plunger 2140 to return immediately to (due to lack of magnetic pull from solenoid 2130) to its original state, further pressing micro switch 2110, and closing electrical path thru electrical connections 2130. Once this electrical path is closed, the generator's engine will be shut down. De-energizing the solenoid is caused either by a high level of toxic gases detected and proper reaction of safety device 2000, shutting down the gas engine, or by a problem with the generator stopping to generate power. This is an additional safety feature, which will shut down the engine in case that the generator will stop generating power. If everything is normally operating, such as no high levels of toxic gases, generator is fully functional, etc, then solenoid 2130 will be continuously energized. Note that once solenoid 2130 is de-energized as explained above, return of plunger 2140 to its resting position will also push outwards knob 2190 to its "STOP" state. Under normal operating conditions, and with solenoid 2130 energized, (generator is running) by pulling on knob 2190 (away from housing 2100), plunger will be released from its magnetically pulled state, and micro switch 2110 will be pushed, initiating a generator shutdown as explained above. This is the manual STOP function, implemented pulling of knob 2190.

Figure 24:
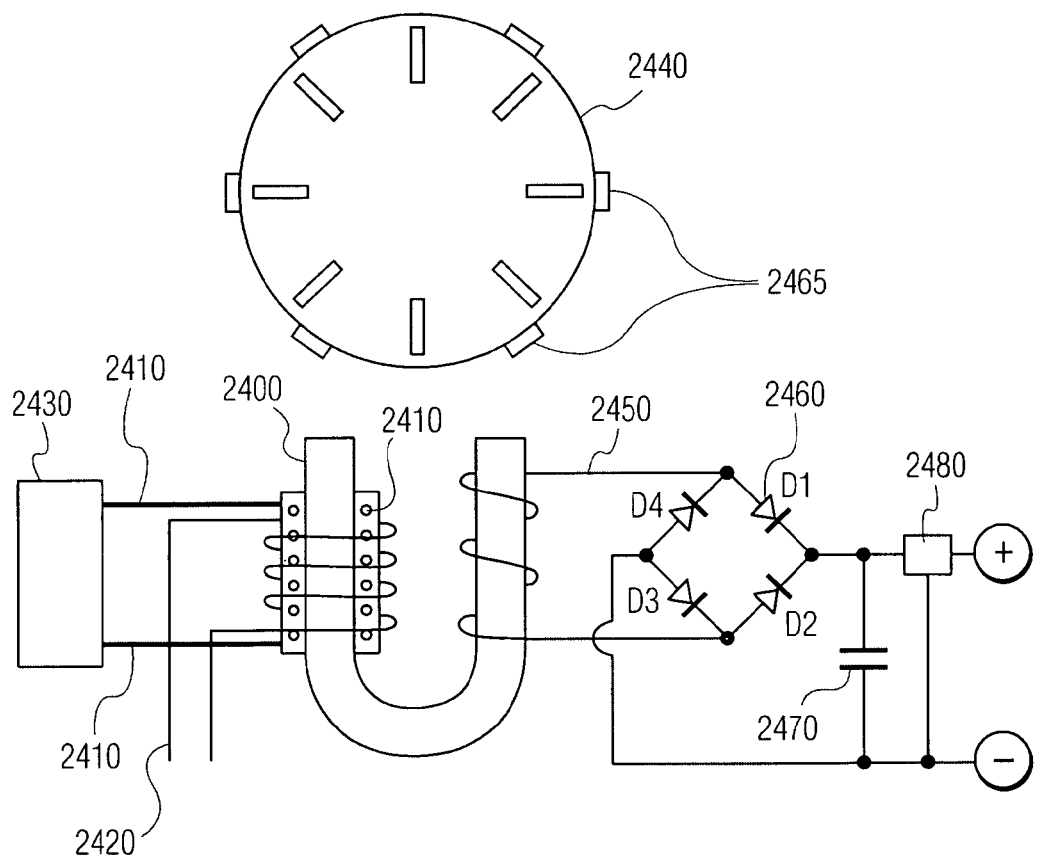
FIG. 24 shows a system for generating power for a safety device from the magneto of the ignition system of a gas engine.

FIG. 24 shows how to generate power for the safety device from the magneto (or generator) used in the ignition system of a typical small gas engine. It may be convenient to power up the safety device from the ignition system rather than from the power generated by the alternator. This may be the case of certain appliances, such as snow throwers, where power is not being generated, and a small gas engine is used.

A magneto is basically an electrical generator that has been tuned to create a periodic high-voltage pulse rather than continuous current. An electrical generator (or a magneto) is the reverse of an electromagnet. In an electromagnet there is a coil of wire around an iron bar (the armature). When current is applied to the electromagnet's coil (e.g. with a battery), the coil creates a magnetic field in the armature. (In a generator, the process is reversed; a magnet moves past the armature to create electric current in the coil.) A magneto consists of the following parts: An armature 2400, normally shaped like a capital "U". The two ends of the U point toward the flywheel 2440. A primary coil 2410 (which may have 200 turns) of thicker wire is wrapped around one leg of the U. A secondary coil 2420 (which may have 20,000 turns of thinner wire wrapped around the primary coil). An electronic control unit that may include ignition module 2430 and/or a set of breaker points and a capacitor. A plurality of permanent magnets 2465 are embedded in the engine's flywheel 2440. When the magnets 2440 fly past the U-shaped armature 2400, they induce a magnetic field in the armature. This field induces some small amount of current in the primary coil 2410 and secondary coil 2420. A sufficiently high voltage should be used, so that as the magnetic field in the armature reaches its maximum, a switch in the electronic control unit 2430 opens. This switch breaks the flow of current through the primary coil and causes a voltage spike (such as 200 volts). The secondary coil, 2420, having 100 times more turns than the primary coil, amplifies this voltage to approximately 20,000 volts, and this voltage feeds to the spark plug. By adding a third winding 2450 to the armature 2400, part of the magnetic field present in the armature, is induced into this coil, presenting an alternating current AC at the output terminals of winding 2450. By feeding this AC voltage to full bridge rectifier formed by diodes D1, D2, D3, and D4 in diode bridge 2460, a direct current DC voltage is obtained. Capacitor 2470 is used to filter the DC voltage output by bridge 2460. Voltage regulator 2480 regulates the output DC voltage from full bridge to a desired voltage needed to operate the safety device.

Figure 25:
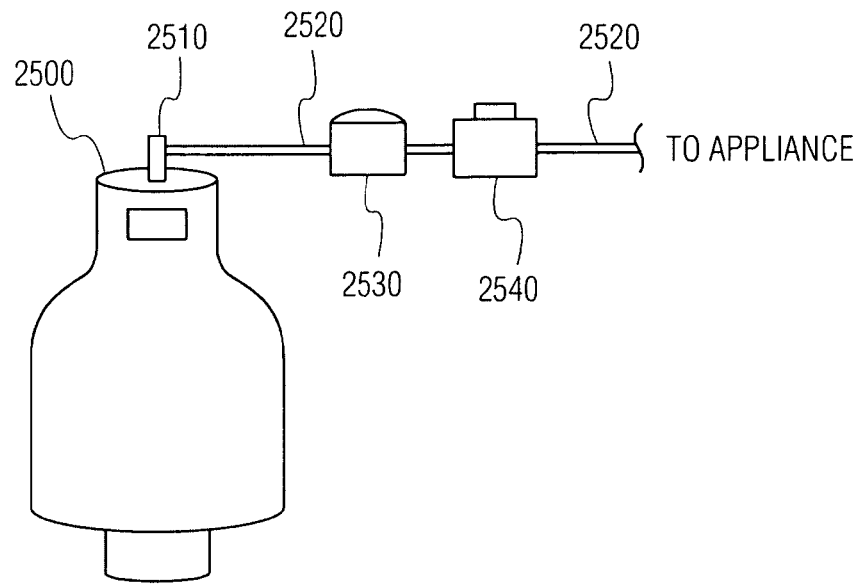
FIG. 25 shows a safety device for alarming and controlling devices using tanks of toxic gas such as a fossil fuel.

FIG. 25 shows a safety device to alarm and control the source of toxic gases in appliances that use, for example, tanks of propane gas, such as those used in portable space heaters, BBQs, etc. Tank of gas 2500 may be a liquefied fossil fuel, propane, or other flammable gas. When the gas in its liquefied state leaves the tank it changes into a gas state, which is used for cooking, heating, etc. These types of appliances generally should not be used in confined spaces since their combustion depletes oxygen and generates toxic gases, such as carbon monoxide. It is an intention of this embodiment of the invention to detect, alarm, and shut down the flow of gas to the appliance in case that the levels of toxic gases reaches dangerous levels. Gas tank 2500 connects to a flexible hose 2520 thru shut off valve 2510. The pressure inside the gas tank is much higher than the pressure needed by the appliance, and also this pressure fluctuates depending on the volume of gas contained in the tank, being the highest when the tank is filled up to maximum capacity. Gas pressure regulator 2530 reduces high-pressure gas in a cylinder or process line to a lower, usable level as it passes to another piece of equipment. It may also serve to maintain pressure within a system. However, the regulator is not a flow control device. It is used to control delivery pressure only. There are three basic operating components in most regulators: a loading mechanism, a sensing element, and a control element. These three components work together to accomplish pressure reduction. The loading mechanism determines the setting of the regulator delivery pressure. Most regulators use a spring as the loading mechanism. When the regulator hand knob is turned, the spring is compressed. The force that is placed on the spring is communicated to the sensing element and the control element to achieve the outlet pressure. The sensing element senses the force placed on the spring to set the delivery pressure. Most regulators use a diaphragm as the sensing element. The diaphragms may be constructed of elastomers or metal. The sensing element communicates this change in force to the control element. The control element is a valve that actually accomplishes the reduction of inlet pressure to outlet pressure. When the regulator hand knob is turned, the spring (loading mechanism) is compressed. The spring displaces the diaphragm (sensing element). The diaphragm then pushes on the control element, causing it to move away from the gas pressure regulators' seat. The orifice becomes larger in order to provide the flow and pressure required. Safety device 2540 is placed inline between the pressure regulator and the appliance's gas connecting line, 2520.

Figure 26:
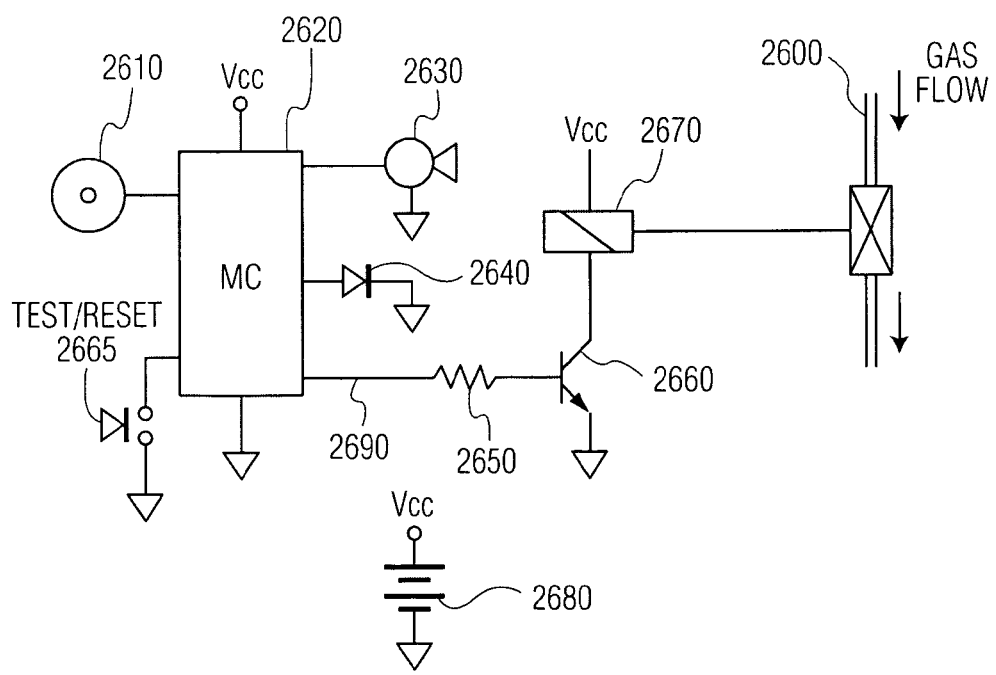
FIG. 26 shows an embodiment of the invention to control devices operated by tanks of a toxic gas, such as a fossil fuel, using a commercially available CO detector.

FIG. 26 shows an implementation of an embodiment of the invention by using the simplest commercial available CO detector known to the inventor in the market. A safety device of this type may use this CO detector or it may be manufactured as a whole unit. Referring to FIG. 26, microcontroller 2620 polls the CO sensor 2610, and upon determination of dangerous levels of CO (based on specific algorithms as described above) it will accordingly indicate CO level and battery status RED LED 2640 with similar status indication as explained with respect to FIG. 2, as well as audible alarm or buzzer 2630. Output port 2690 from microcontroller 2620 is used as a control signal to actuate a normally closed (NC) electromechanical gas valve 2670. This is a gas valve that needs a voltage pulse in order to open the flow of gas, and it is designed to draw a minimal amount of current (in order to conserve the battery of the safety device) while in the OPEN holding state. Such type of valves are readily available. It is important to note that in the absence of power, whether caused by low or removed batteries, this valve will be normally closed and the gas flow 2600 is interrupted. In normal operating conditions, and in the absence of toxic levels of CO, control signal 2600 is high, allowing the flow of gas thru gas pipe or hose. If dangerous levels of CO are detected, or TEST/RESET pushbutton 2665 is used to test the unit, microcontroller 2620 under software control, in addition to setting LED 2640 and sounding audible alarm 2630, will set output pin 2690 low. This will cause buffer transistor 2660 thru base current limiting resistor 2650 to go into a non conducting state, causing NC gas valve 2670 to be shut off. In embodiments of this invention, alarm indicator LED 2640, audible buzzer 2630, and gas valve relay 2670 can be returned to their normal operating condition by depressing TEST/RESET pushbutton 2665 and by properly ventilating the area in case that the system detected high levels of CO.

TEST/RESET pushbutton 2665 has a double function, as in some of the commercial CO alarm units. If the safety device is in a non-alarm mode (no dangerous levels of CO detected) by depressing TEST/RESET pushbutton will cause microcontroller 2620 to simulate an alarm, and go into an alarm, as explained above; it will also shutdown the gas valve. If the safety device was in an alarm state, depressing TEST/RESET pushbutton will ONLY disable the audible alarm, but it will not reopen the gas valve. The additional software functions used to actuate the electromechanical gas valve 2670 as explained here are minor software additions to the existing software running microcontroller 2620 are discussed above.

It will be understood that the above-described embodiments are merely illustrative of the principles of the invention and that other arrangements may be devised by those skilled in the art without departing from the spirit and scope of the invention.

What is claimed is:

1. An electromechanical switch comprising:
   (a) a plunger;
   (b) a first switch in contact with said plunger in a first position of said plunger, in which a connection of said switch is open;
   (c) a button in sliding contact with said plunger;
   (d) a solenoid in contact with said plunger in a second position of said plunger, in which a connection of said first switch is closed; and
   (e) a holding element in said plunger in contact with an engaging element in a third position of said plunger, in which said plunger is not in contact with said first switch and is not in contact with said solenoid, and a connection of said first switch is closed.

2. The electromechanical switch of claim 1 in which said first switch is coupled to a relay.

3. The electromechanical switch of claim 1 in which said first switch is coupled to a normally closed switch.

4. The electromechanical switch of claim 1 wherein said holding element is a notch.

5. The electromechanical switch of claim 1 wherein said engaging element is a lever.

* * * * *